(12) United States Patent
Sjostedt et al.

(10) Patent No.: US 8,437,855 B2
(45) Date of Patent: May 7, 2013

(54) CONNECTOR ASSEMBLY FOR USE WITH MEDICAL DEVICES

(75) Inventors: Robbie J. Sjostedt, Foothill Ranch, CA (US); Farshid Dilmaghanian, Rancho Santa Margarita, CA (US); Majid Ghasiri, Mission Viejo, CA (US); Steve Twork, Lake Forest, CA (US); Jay Huang, Huntington Beach, CA (US)

(73) Assignee: Bal Seal Engineering, Inc., Foothill Ranch, CA (US)

( * ) Notice: Subject to any disclaimer, the term of this patent is extended or adjusted under 35 U.S.C. 154(b) by 1433 days.

(21) Appl. No.: 12/062,895

(22) Filed: Apr. 4, 2008

(65) Prior Publication Data

US 2008/0246231 A1    Oct. 9, 2008

Related U.S. Application Data

(60) Provisional application No. 60/910,765, filed on Apr. 9, 2007, provisional application No. 60/911,161, filed on Apr. 11, 2007, provisional application No. 61/024,660, filed on Jan. 30, 2008.

(51) Int. Cl.
*A61N 1/3752* (2006.01)

(52) U.S. Cl.
USPC ............... 607/37; 439/668; 439/827; 29/876

(58) Field of Classification Search .............. 607/37; 439/668, 827; 29/876
See application file for complete search history.

(56) References Cited

U.S. PATENT DOCUMENTS

| | | |
|---|---|---|
| 4,072,154 A | 2/1978 | Anderson et al. |
| 4,105,037 A | 8/1978 | Richter et al. |
| 4,202,592 A | 5/1980 | Rullier et al. |
| 4,262,673 A | 4/1981 | Kinney et al. |
| 4,461,194 A | 7/1984 | Moore |
| 4,934,366 A | 6/1990 | Truex et al. |
| 4,934,367 A | 6/1990 | Daglow et al. |
| 5,012,807 A | 5/1991 | Stutz, Jr. |
| 5,413,595 A | 5/1995 | Stutz, Jr. |
| 5,817,984 A | 10/1998 | Taylor et al. |
| 5,866,851 A | 2/1999 | Taylor et al. |
| 6,029,277 A | 2/2000 | Picchione, II |
| 6,141,205 A | 10/2000 | Nutzman et al. |
| 6,192,277 B1 | 2/2001 | Lim et al. |
| 6,428,368 B1 | 8/2002 | Hawkins et al. |
| 6,498,952 B2 | 12/2002 | Imani et al. |
| 6,671,554 B2 | 12/2003 | Gibson et al. |
| 6,878,013 B1 | 4/2005 | Behan |

(Continued)

OTHER PUBLICATIONS

First Examination Report dated Jul. 8, 2011 from corresponding European Application No. 08745235.5 (4 pages).

(Continued)

*Primary Examiner* — Christopher D Koharski
*Assistant Examiner* — Michael Carey
(74) *Attorney, Agent, or Firm* — Klein, O'Neill & Singh, LLP

(57) ABSTRACT

Connector assemblies for use with implantable medical devices having easy to assemble contacts are disclosed. The connector assemblies are generally formed by coupling a plurality of ring contacts, sealing rings, and spring contact elements together with at least one holding ring to form a connector having a common bore fore receiving a medical lead cable. Contact grooves or spring chambers for positioning the spring contact elements are formed in part by assembling multiple components together.

30 Claims, 15 Drawing Sheets

U.S. PATENT DOCUMENTS

| | | | |
|---|---|---|---|
| 6,879,857 B2 | 4/2005 | Swanson et al. | |
| 6,895,276 B2 * | 5/2005 | Kast et al. | 607/37 |
| 7,003,351 B2 | 2/2006 | Tvaska et al. | |
| 7,047,077 B2 | 5/2006 | Hansen et al. | |
| 7,062,329 B2 | 6/2006 | Ostroff | |
| 7,063,563 B1 | 6/2006 | Hsu | |
| 7,070,455 B2 | 7/2006 | Balsells | |
| 7,083,474 B1 * | 8/2006 | Fleck et al. | 439/668 |
| 7,108,549 B2 | 9/2006 | Lyu et al. | |
| 7,164,954 B2 | 1/2007 | Lefebvre et al. | |
| 7,187,974 B2 | 3/2007 | Haeg et al. | |
| 7,195,523 B2 * | 3/2007 | Naviaux | 439/827 |
| 7,241,180 B1 | 7/2007 | Rentas Torres | |
| 7,263,401 B2 | 8/2007 | Scott et al. | |
| 7,299,095 B1 | 11/2007 | Barlow et al. | |
| 7,303,422 B2 | 12/2007 | Hoffer et al. | |
| 7,326,083 B2 | 2/2008 | Mehdizadeh et al. | |
| 7,429,199 B2 | 9/2008 | Burgess | |
| 2005/0186829 A1 * | 8/2005 | Balsells | 439/352 |
| 2006/0047322 A1 * | 3/2006 | Naviaux | 607/37 |
| 2006/0095086 A1 | 5/2006 | Balsells | |
| 2006/0224208 A1 | 10/2006 | Naviaux | |
| 2009/0048638 A1 | 2/2009 | Rey et al. | |

OTHER PUBLICATIONS

Extended European Search Report mailed Oct. 4, 2010 from corresponding European Application No. 08745235.5, filed Sep. 18, 2009 (7 pages).

International Search Report completed and mailed Aug. 18, 2008 from corresponding PCT Patent Application No. PCT/US2008/059568, filed Apr. 7, 2008 (3 pages).

Written Opinion completed and mailed Aug. 18, 2008 from corresponding PCT Patent Application No. PCT/US2008/059568, filed Apr. 7, 2008 (3 pages).

Preliminary Report completed and mailed Oct. 13, 2009 from corresponding PCT Patent Application No. PCT/US2008/059568, filed Apr. 7, 2008 (6 pages).

* cited by examiner

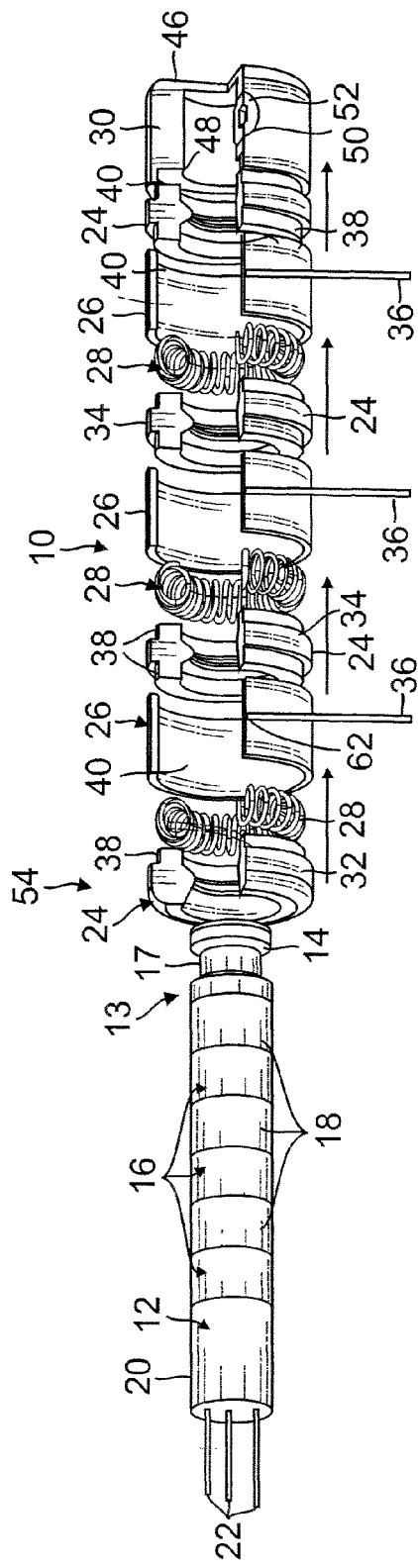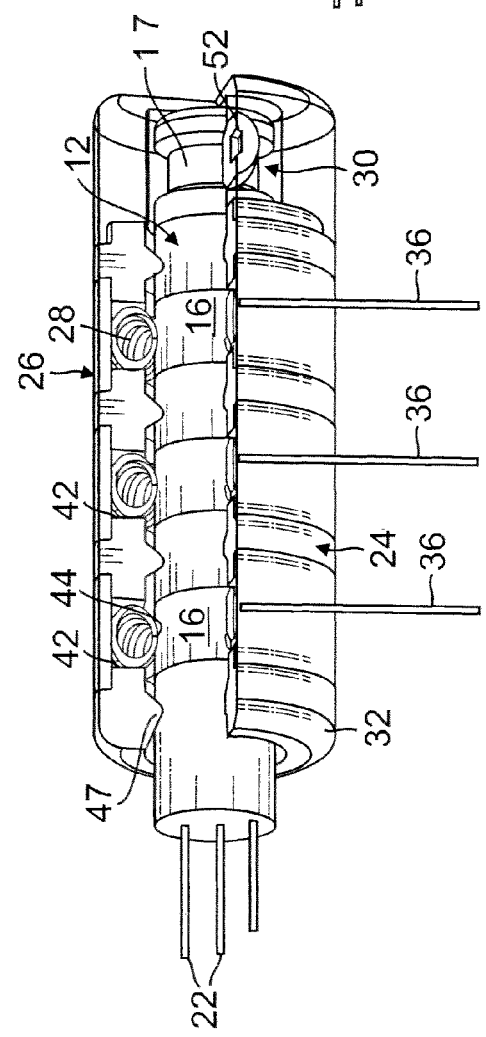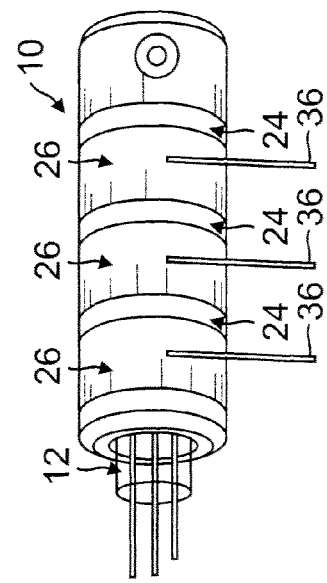

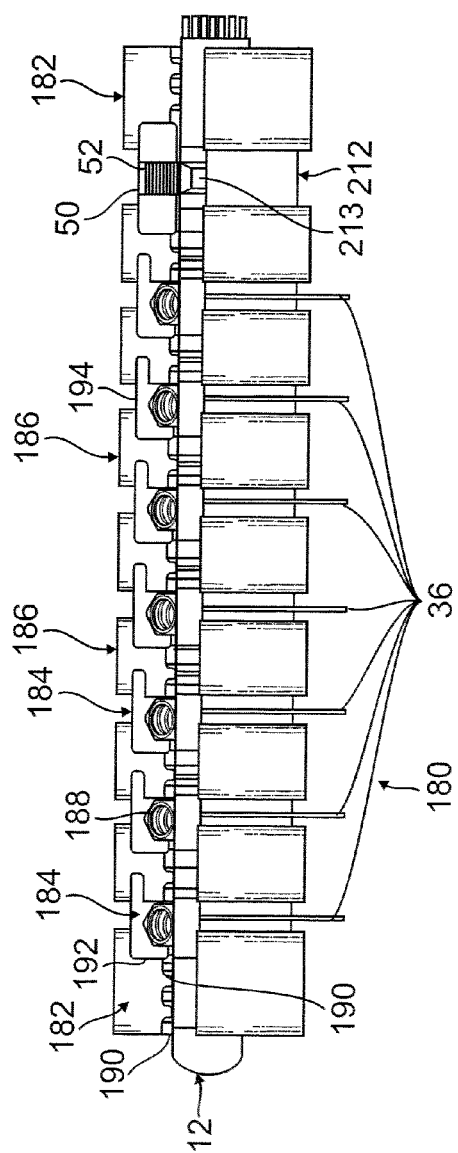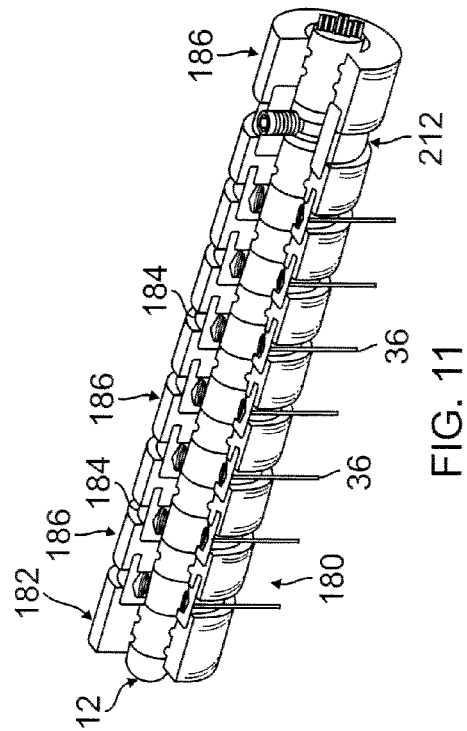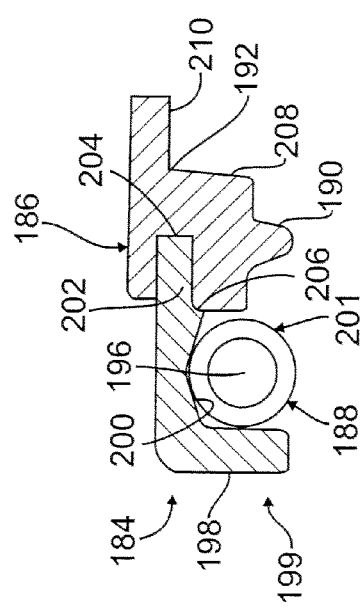

CONNECTOR ASSEMBLY FOR USE WITH MEDICAL DEVICES

CROSS-REFERENCE TO RELATED APPLICATIONS

This is an ordinary application of provisional application No. 60/910,765, filed Apr. 9, 2007, entitled Connector Assembly for Use with Medical Devices; of provisional application No. 60/911,161, filed Apr. 11, 2007, entitled Integrated Header Connector System; and of provisional application No. 61/024,660, filed Jan. 30, 2008, entitled In-Line Connectors; the contents of each of which are expressly incorporated herein by reference as if set forth in full.

A connector assembly having one or more conductive elements in spaced-apart configuration is generally discussed herein with particular discussions extended to connector assemblies for use with implantable medical devices having easy to assemble contact elements.

BACKGROUND

Implantable medical devices for providing electrical stimulation to body tissues, for monitoring physiologic conditions, and for providing alternative treatments to drugs are well known in the art. Exemplary implantable medical devices include implantable cardio defibrillators, pacemakers, and programmable neuro-stimulator pulse generators, which are collectively herein referred to as "implantable medical devices" or IMDs. These IMDs typically incorporate a hermetically sealed device enclosing a power source and electronic circuitry. Connected to the sealed housing, also known as a "can," is a header assembly. The header assembly includes electrical contact elements that are electrically coupled to the electronic circuits or to the power source located inside the can via conductive terminals or leads. The header assembly provides a means for electrically communicating, via an external medical lead cable, between the electronic circuits or power source located inside the device and the actual stimulation point.

Industry wide standards have been adopted for, among other things, the dimensions, size, pin spacing, diameter, etc. for the receptacle and the medical lead cable. Furthermore, good electrical contact must be maintained during the life of the implantable medical device, and the medical lead cable for use with the IMD must not disconnect from the receptacle located in the header, yet be detachable for implanting and programming purposes and for replacing the IMD when necessary.

Although prior art connector contacts provide viable options for medical device manufacturers, the overall dimensions of existing receptacles pose manufacturing challenges. Among other things, placing stackable rings in between electrically insulating seals, positioning conductive contact elements in between conductive grooves for forming a receptacle and integrating the contact assembly into the IMD are difficult, costly and time consuming tasks. Accordingly, there is a need for a receptacle that not only meets the challenges associated with implantable applications but is also easier to manufacture than a variety of existing receptacles. There is also a need for a receptacle that is easily adaptable with existing implantable medical devices that are easier to manufacture than a variety of existing implantable medical devices.

SUMMARY

Aspects of the present invention includes an implantable medical device comprising a header attached to a sealed housing. A connector assembly is disposed in the header and comprises a ring contact element having a wall structure comprising an interior wall surface and an exterior wall surface; the ring contact element being electrically conductive. A first seal ring comprising a wall structure comprising an exterior wall surface and an interior wall surface having an annulus comprising an inside diameter; a second seal ring comprising a wall structure comprising an exterior wall surface and an interior wall surface having an annulus comprising an inside diameter; and wherein the first seal ring and the second seal ring overlap the ring contact element such that the exterior wall surface of the ring contact element contacts the interior wall surface of both the first seal ring and the second seal ring. A spring contact element is positioned in a spring chamber formed by the interior wall surface of the ring contact element and two side walls each formed from an electrically insulative material.

Optionally, one of the two side walls of the medical device is defined by the annulus of the first seal ring and the other one of the two side walls is defined by the annulus of the second seal ring.

As provided, the ring contact element may have a generally constant inside diameter throughout the interior wall surface.

A further aspect of the present invention includes modifying the annulus of the first seal ring to have two tapered edges defining a lip.

For a longer connector, a further aspect of the present invention includes incorporating a second ring contact element in contact with the interior wall surface of the first seal ring.

In yet another aspect of the present invention, there is provided an implantable medical device comprising a header attached to a sealed housing and having a connector assembly disposed in the header comprising two ring contact elements each comprising a wall structure comprising an interior wall surface and an exterior wall surface; the two ring contact elements being electrically conductive. A seal ring comprising a wall structure comprising an exterior wall surface and an interior wall surface having an annulus comprising an inside diameter is incorporated wherein the seal ring overlaps the two ring contact elements such that the exterior wall surfaces of the two ring contact elements each contacts the interior wall surface the seal ring. The two spring chambers, each comprising a back wall and two side walls, are defined, at least in part, by the interior wall surfaces of the two ring contact elements and the annulus of the seal ring.

In accordance with aspects of the present invention, the seal ring is may be made from an electrically insulative material.

In yet another aspect of the present invention, a connector assembly is provided comprising a first end seal near an opening to the connector assembly; a second end seal on an end of the connector assembly opposite the first end seal; a plurality of ring contact elements disposed in between the first end seal and the second end seal; and a plurality of seal rings disposed in between the first end seal and the second end seal. At least one of the ring contact elements is disposed in between two seal rings and in sealing arrangement with the two seal rings. The plurality of ring contact elements each comprises a centerline along a radial direction, which divides the ring contact element into a first ring section and a second ring section, and wherein the first ring section and the second ring section are not symmetrical.

In yet another aspect of the present invention, there is provided a method for forming a cavity for retaining a spring in a connector for a medical device comprising providing an electrically conductive ring contact element comprising a wall surface, a groove, and a single side wall singularly formed with the wall surface, said single side wall covering a first side of the groove; placing an electrically insulative seal ring in adjacent contact with the electrically conductive ring contact element; said seal ring providing a wall surface for a second side of the groove; placing a spring into the groove; and wherein the spring is retained by the single side wall and the wall surface of the seal ring such that the spring is restricted along an axial direction by the single side wall and the wall surface.

An additional aspect of the present invention is an implantable medical connector stack having easy to install ring grooves for receiving contact springs comprising: a first seal element made of a dielectric material comprising an annulus comprising a projection; said annulus comprising a generally planar wall surface; a conductive ring contact element comprising an interior wall surface adjacent at least one axial opening; a second seal element made of a dielectric material comprising an annulus comprising a projection; a canted coil spring; wherein the conductive ring contact element is engaged to the first seal element and the second seal element and a ring groove is formed by at least one of said engagements; and wherein the generally planar wall surface of the first seal element forms a dielectric side wall of the ring groove that together with the interior wall surface of the conductive ring contact element define a physical stop for retaining the canted coil spring inside the ring groove.

A still additional aspect of the present invention is an implantable medical connector stack having easy to install ring grooves for receiving contact springs comprising: a conductive ring contact element comprising a first axial side and a second axial side; a first dielectric seal element in mechanical engagement with the first axial side of the conductive ring contact element; a second dielectric seal element in mechanical engagement with the second axial side of the conductive ring contact element; and wherein a ring groove for accommodating a canted coil spring is formed by the engagements between the conductive ring contact element and the first and second dielectric seal elements; and wherein at least part of the ring groove has a first side wall formed by at least one of the first dielectric seal element and the second dielectric seal element.

Aspects of the present invention further includes a method for forming an implantable medical connector stack having easy to install ring grooves for receiving contact springs. In one embodiment, the method comprises the steps of positioning a canted coil spring into a conductive ring contact element; positioning the conductive ring contact element into engagement with a first dielectric seal element; positioning the conductive ring contact element into engagement with a second dielectric seal element; wherein a groove comprising a bottom wall and two side walls is formed by the engagement between the conductive ring contact element and at least one of the first and second dielectric seal elements; and wherein at least one of the two side walls is formed by part of the first dielectric seal element or the second dielectric seal element.

An additional aspect of the present invention is a method for forming an implantable medical connector stack having easy to install ring grooves for receiving contact springs. The method comprises: forming a ring groove by sliding a conductive ring contact element and two dielectric seal elements onto an installation rod and into axial engagement with one another; and placing a canted coil spring into the ring groove by placing the canted coil spring onto the installation rod and sliding the canted coil spring under a bottom wall defined by the conductive ring contact element.

In yet another aspect of the present invention, there is provided a method for forming an implantable medical connector stack having easy to install ring grooves for receiving contact springs. The method comprising: projecting two axial ends of a conductive ring contact element over two shoulders of two adjacent non-conducting seal elements or under two shoulders of two adjacent dielectric seal elements to form a ring groove comprising a bottom wall made of a conductive material and two side walls each made from a non-conductive material; and placing a canted coil spring into the ring groove before the conductive ring contact element projects over or under at least one of the two adjacent non-conducting seal elements.

In still yet other aspect of the present invention, a method for forming a connector stack for an implantable medical device having reduced overall length is provided. The method comprising inserting a tubular ring contact element into two adjacent seal ring elements to form a ring groove, and placing a spring into said ring groove.

Other aspects and variations of the connector assemblies summarized above are also contemplated and will be more fully understood when considered with respect to the following disclosure.

BRIEF DESCRIPTION OF THE DRAWINGS

FIG. 1 is an exploded isometric cut-away view of a connector assembly provided in accordance with aspects of the present invention, which comprises a plurality of seal rings, contact rings, and spring contact elements.

FIG. 2 is an isometric cut-away view of the connector assembly of FIG. 1 in an assembled state with a medical lead cable disposed in the connector bore.

FIG. 3 is an isometric view of the connector assembly of FIG. 2.

FIGS. 10-11 show yet another alternative connector assembly in accordance with aspects of the present invention.

Figure 4:
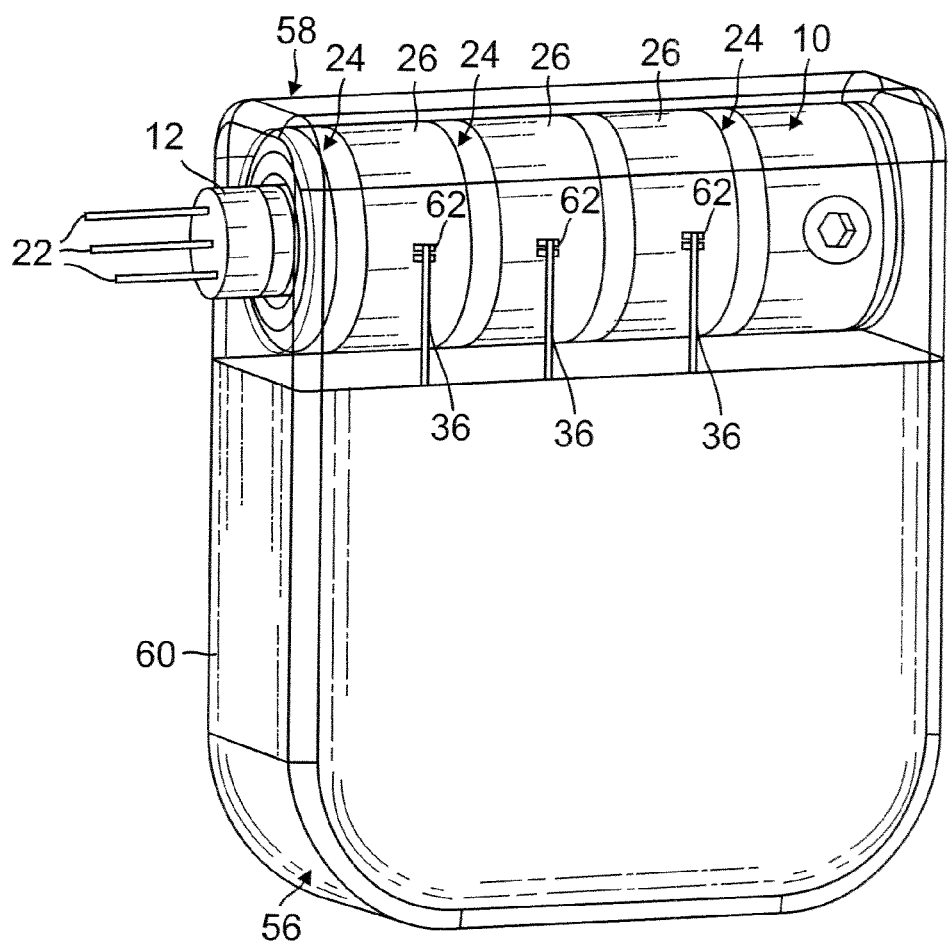
FIG. 4 is an isometric transparent view of the connector assembly of FIGS. 1-3 inside a header and atop a sealed housing of an implantable medical device.

Other aspects and features of the receptacles provided herein may be better appreciated as the same become better understood with reference to the specification and claims.

DETAILED DESCRIPTION

The detailed description set forth below in connection with the appended drawings is intended as a description of the presently preferred embodiments of connector assemblies or stacks for electrically communicating with medical leads or conductive terminals. The leads in turn connect to integrated circuits, a power source, and/or circuit chips located inside a sealed medical implantable device. The connector assemblies provided in accordance with aspects of the present invention are not intended to represent the only forms in which the present invention may be constructed or utilized. The description sets forth the features and the steps for constructing and using the connector assemblies of the present invention in connection with the illustrated embodiments. It is to be understood that the same or equivalent functions and structures may be accomplished by different embodiments and are also intended to be encompassed within the spirit and scope of the present invention, especially those incorporating a combination of features shown in the different embodiments included herein. As denoted elsewhere herein, like element numbers are intended to indicate like or similar elements or features.

Referring now to FIG. 1, an exploded isometric cut-away view of a connector assembly or implantable medical connector stack provided in accordance with aspects of the present invention is shown, which is generally designated 10. The connector assembly 10 is configured to receive a medical lead cable 12, which has a proximal end 13 comprising a proximal tip 14, having a recessed section or groove 17 for accepting a set screw or other lead locking device, and a plurality of electrical terminals 16 interposed in between lead insulators 18. The lead cable 12 further comprises a lead body 20 for carrying a plurality of electrode leads 22 from between the proximal end 13 and a distal end (not shown), which has electrode terminals for providing electrical stimulation to the body tissues. The number of electrode leads 22 and corresponding number of electrical terminals 16 can vary depending on the particular implant application, which also determines the number of electrical ring contacts in the connector assembly 10, as further discussed below. Accordingly, applications of the connector assemblies discussed herein include unipolar, bipolar, and multi-polar applications by simply changing the number of components used to make the connector assembly.

In one exemplary embodiment, the connector assembly 10 comprises a plurality of non-conductive seal rings 24, conductive ring contact elements 26, and spring contact elements 28. Together with a holding ring 30, the plurality of seal rings 24, ring contact elements 26, and spring contact elements 28 form the basic components of the connector assembly 10 of the present embodiment, which has a common bore for receiving the proximal end of the lead cable 12. Broadly speaking, the seal rings 24 are each configured to seal, along its internal diameter, against the lead cable 12 and, along the outer periphery of its exterior shoulders, adjacent ring contact element(s) 26. As is readily apparent to a person of ordinary skill in the art, bodily fluids should be prevented from traveling along the lead cable 12 into the connector assembly or in through the seams between the contact ring element 26 and two adjacent seal rings 24. The ring contact elements 26 are each configured to pass an electric current or signal from a conductor 36 located inside an IMD housing to a corresponding spring contact element 28, which then passes the electric current or signal to a corresponding electrical terminal 16 on the lead cable 12 then onto a corresponding electrode lead 22 located inside the lead body 20 and to a corresponding electrode terminal on the distal end of the lead cable. The same function is accomplished when the connector contacts are used as an Extension, which is the primary electrical connection used during implant surgery.

In accordance with aspects of the present invention, two sub-classes of seal rings 24 are incorporated, which include an end seal ring 32 and an intermediate seal ring 34. The end seal ring 32 comprises a single external shoulder 38 for projecting into an adjacent bore 40, which could be that of a contact ring 26 or otherwise. The intermediate seal ring 34 comprises two external shoulders 38 for projecting into two adjacent bores 40, which could be that of two different contact rings 26 or otherwise, such as one contact ring 26 and a holding ring 30. However, an intermediate seal ring 34 can be used in place of an end seal ring 32 without deviating form the spirit and scope of the present invention.

With reference to FIG. 2 in addition to FIG. 1, when two adjacent seal rings 24 engage the bore 40 of a common contact ring element 26, a contact groove 42 is formed for accommodating a spring contact element 28. The spring contact element 28, which is preferably a radial or axial canted coil spring commercially available along with the seals from Bal Seal Engineering of Foothill Ranch, Calif., is sized so that it is positioned by the groove along its two axial ends and establishes contact along its outer and inner radial circumference. Its internal diameter 44 is preferably smaller than the internal diameter 46 of the seal ring 24, which is slightly smaller than the outer diameter of the proximal end 13 of the lead cable 12. In other words, when the proximal end 13 of the lead cable 12 is inserted into the common bore, the lead cable has a slight interference fit with the plurality of seal rings 24 and the canted coil springs 28. The seal rings 24 are also in interference fit with the adjacent bores along their respective external shoulders 38 to facilitate assembly of the various components.

The spring contacts 28 are similarly sized so that each is deflected by the lead cable 12 to about 5% and up to about 50% of its total radial deflection with up to about 40% being more preferred. This deflection range ensures a sufficient spring contact force is generated between the contract rings 26 and the electric terminals 16 on the lead cable 12 for transferring electric current or signals between the two.

Referring again to FIG. 1, in one exemplary embodiment, the contact rings 26 are each generally cylindrical in configuration. More preferably, each contact ring 26 has a generally constant inner diameter and outer diameter with two square ends, with normal manufacturing tolerance being acceptable. Said differently, the contact rings 26 do not have machined or formed grooves for forming contact grooves therein for accommodating the spring contact elements 28. The contact rings 26 have a simple profile, which in one embodiment is tubular in shape and makes manufacturing the rings and assembling the spring contacts 28 therein easier and therefore more cost effective. The contact grooves are formed instead by a combination of adjacent seal rings 24 and the inner surface of the ring contact element 26. While FIG. 1 is the more preferred design, alternative contact ring internal geometries are possible in the area of contact with the spring without compromising ease of assembly for the spring 28 and contact ring. For example, the contact ring inside diameter can have a "v" shaped groove geometry in the area of the spring contact so that two points of contact are available with the spring versus one.

Other geometries are also contemplated. For example, the contact ring 26 may have a thicker section so that there are at least two internal diameters. The spring contact element 28 can then be inserted through the larger internal diameter end of the contact ring 26 until it abuts the shoulder formed at the intersection between the two different internal diameters. Thus, different diameters and undulating internal surfaces for the contact rings are contemplated. The ring with a v-shaped groove can be considered a sub-species of a ring having at least two internal diameters. Still alternatively, the plurality of contact rings in a single connector assembly may vary, i.e., are not uniform. For example, it is possible to use a ring with a "v" shaped groove at the distal most end of the connector assembly and rings with a smoother contour as shown in FIG. 1 for the remaining contact rings. Still alternatively, a ring with two different internal diameters may be used with the ring having a v-shaped groove and with rings having a uniform internal diameter. If a contact ring having two different internal diameters at its two ends is used, the seal rings 24 are modified accordingly to engage the different internal diameters of the contact ring. Thus, contact rings provided herein not only can have a smooth internal diameter, but also machined surfaces and undulating surfaces.

Thus, in accordance with one aspect of the present invention, there is provided a method for assembling a plurality of components to form a connector assembly or stack comprising engaging a first seal ring 34 to a holding ring 30, engaging a first contact ring 26 with the first seal ring 34, placing a first spring contact element 28 inside the first contact ring, and engaging a second seal ring 34 with the first contact ring to form a ring groove for constraining the first spring contact therein. The method further comprises steps that include adding other seal rings, contact rings, and spring contact elements to form a connector assembly having a desired number of contact grooves. More preferably, the method further comprises the steps of assembling a connector assembly without having to utilize a tool or by hand or by secondary assembly processes manipulate, compress, bend, or distort a spring contact to fit within a contact groove. The assembled connector assembly is typically then placed into a mold cavity and over-molded with an implantable grade polymer or elastomer, such as epoxy or silicone. The connector assembly can also be inserted into a pre-molded header, which resembles a housing having a cavity for receiving the connector assembly and one or more openings for placing the connector assembly into the pre-molded header. The one or more openings are then backfilled or sealed, typically after attaching or welding the conductors from the sealed housing to the contact rings, to complete the assembly.

In accordance with other aspects of the present invention, there is provided an alternative method for assembling a connector assembly in which a dowel or assembly pin (not shown) is used, which resembles the proximal end 13 of the lead cable 12 shown in FIG. 1. The assembly pin (not shown) is used to construct the connector assembly 10 by first placing a holding ring 30 on an end of the assembly pin and then subsequently placing other components on the pin and then sliding them into engagement with the earlier placed components. The assembled components, i.e., the connector assembly or stack, may then be secured by placing the same inside a cavity and over-molding the assembly with an implantable grade polymer or elastomer.

In the embodiment shown, the holding ring 30 functions as an end cap and has an end wall 46 and a shoulder 48 for mating engagement with the shoulder on the seal ring 34. A threaded bore 50 for receiving a set screw 52 is incorporated in the holding ring 30 to more securely fixing the lead cable 12 to the connector 10 assembly (FIG. 2). Alternatively, an end holding ring (not shown) may be incorporated at the distal most end 54 of the connector assembly for providing the locking function on the lead cable 12. During the over-molding step, a window should be formed around the threaded bore 50 for securing the lead cable, which can then be back-filled using a curable and implantable material.

Referring again to FIG. 2, the seal rings 24 of the present embodiment, except for the end seal ring 32, are each symmetrical about a centerline drawn perpendicular to the axis defined by the lead cable 12 and through the center of the seal ring. However, non-symmetry or other configurations are possible so long as a contact groove for accommodating a spring contact is formed at least in part by engaging the contact ring 26 with two adjacent seal rings 24. Furthermore, while the seal rings 24 of the present embodiment are shown each comprising an internal projection 47 for sealing against the lead cable 12, as previously discussed, two or more projections may be incorporated without deviating from the spirit and scope of the present invention. Still furthermore, part of the seal ring that projects into the bore of a contact ring can be made separately. In other words, a seal ring may be made by co-molding or over-molding two separate components.

Following assembly of the various components to form the connector assembly 10 shown in FIG. 2, the connector assembly is encased inside an implantable elastomer or polymer layer, as previously discussed. The connector assembly 10 is preferably molded with an assembly pin located inside the common bore to ensure alignment, both radially and axially, of the various connector components. The encased connector may be referred to as a connector header, for placing on a can or sealed housing of an IMD. In one exemplary embodiment, windows (not shown) are left exposed through the over-molded layer adjacent each contact ring 26. When the header is placed over the can, a plurality of contact conductors 36 in communication with a power source and/or electronic circuits inside the can project upwardly into physical contact with the contact rings 26. The contact conductors 36 may then welded to a corresponding contact ring 26 to ensure good electrical contact through the windows. The windows are then backfilled and sealed using curable implantable elastomer or polymer.

FIG. 3 is a fully assembled view of the connector assembly 10 of FIGS. 1 and 2 with the medical lead cable 12 disposed inside the common bore. As can be appreciated, the connector stack 10 provided herein allows for the distance between one ring contact element and an adjacent ring contact element to be reduced. The reduction is facilitated by, among other things, eliminating metallic side walls for capturing the springs inside the ring grooves. Thus, the overall length of the stack, from the holding ring 30 to the distal end most seal element 24, may be reduced compared to connector stacks having metallic side walls for capturing the springs. Accordingly, a method is provided for forming a connector stack having reduced overall length comprising inserting a tubular ring into two adjacent seal ring elements to form a ring groove, and placing a spring into said ring groove. Advantageously, the stack provided in accordance with aspects of the present invention reduces manufacturing and installation costs, simplifies assembly, and shortens the overall length of the stack to allow for smaller sized IMDs.

Referring now to FIG. 4, an IMD 56 incorporating a connector assembly 10 provided in accordance with aspects of the present invention is shown. The connector assembly 10 is shown in a header 58, which is shown as a transparent material or structure for purposes of discussion. In practice, the overcoat or over-molding layer is more commonly semi-opaque or opaque. The header 58 is situated over a can 60, which is hermetically sealed with a power source and electronic circuits. As previously discussed, the IMD can be any one of plurality of IMDs for medical treatment, monitoring, or diagnostics.

Also shown in FIG. 4 are weld traces 62 for welding the conductors 36 to the contact rings 26. Typically, the conductors 36 project through one or more feed through terminals that pass through the hermetically sealed housing or can 60 to contact the contact rings 26. Although a single connector assembly 10 is shown inside the header 58, two or more connector assemblies 10 may be used if desired depending on the particular implant application. The connector assemblies may be stacked side-by-side or on top of one another.

Figure 5:
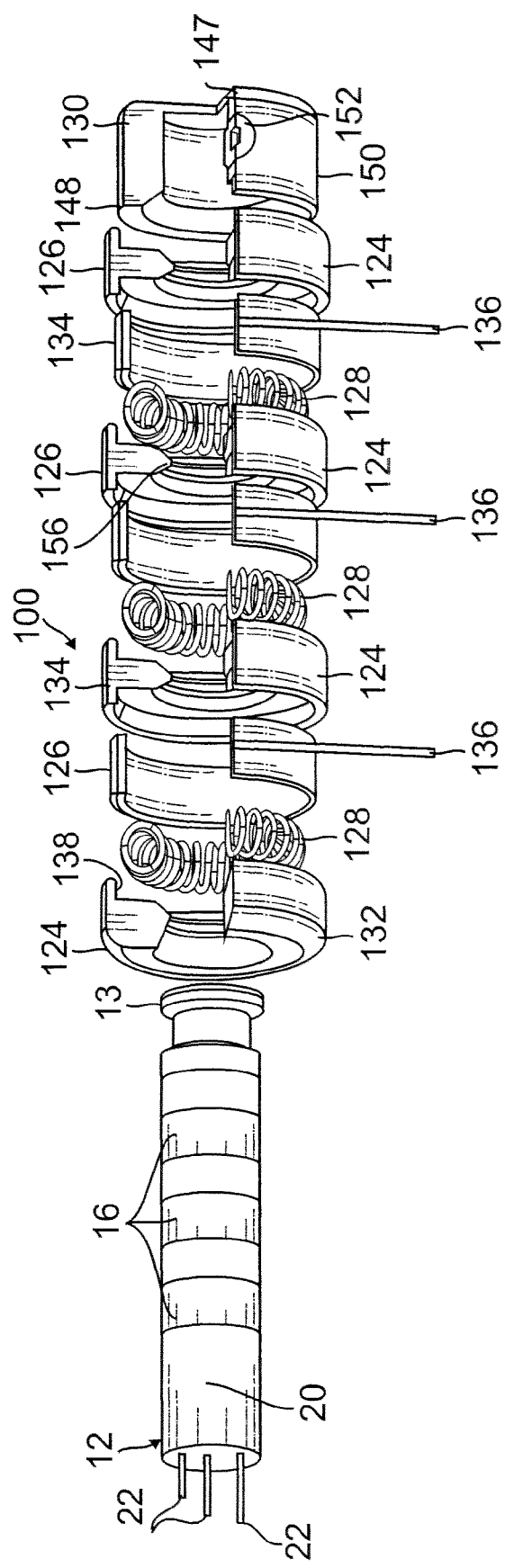
FIG. 5 is an exploded isometric cut-away view of an alternate embodiment of a connector assembly provided in accordance with aspects of the present invention, which comprises a plurality of seal rings, contact rings, and spring contact elements.

With reference now to FIG. 5, in another exemplary embodiment, a connector assembly 100 comprises a plurality of non-conductive seal rings 124, conductive ring contact elements 126, and spring contact elements 128. Together with a holding ring 130, the plurality of seal rings 124, ring contact elements 126, and spring contact elements 128 form the basic components of the connector assembly 100 of the present embodiment, which has a common bore for receiving the proximal end of the lead cable 12. Generally speaking, the seal rings 124 provide a seal along their interior bore 156 when compressed against the lead cable 12, and along the inner periphery of their interior shoulders 138 against adjacent ring contact element(s) 126. As is readily apparent to a person of ordinary skill in the art, bodily fluids should be prevented from traveling along the lead cable 12 into the connector assembly or in through the seams between the ring contact elements 126 and adjacent seal rings 124. The ring contact elements 126 are each configured to pass an electric signal from a lead 136 having one end located inside an IMD housing to a corresponding spring contact element 128, which then passes the electric signal to a corresponding electrical terminal 16 on the lead cable 12, then onto a corresponding electrode lead 22 located inside the lead body 20 and to a corresponding electrode terminal on a distal end of the lead cable.

Figure 6:
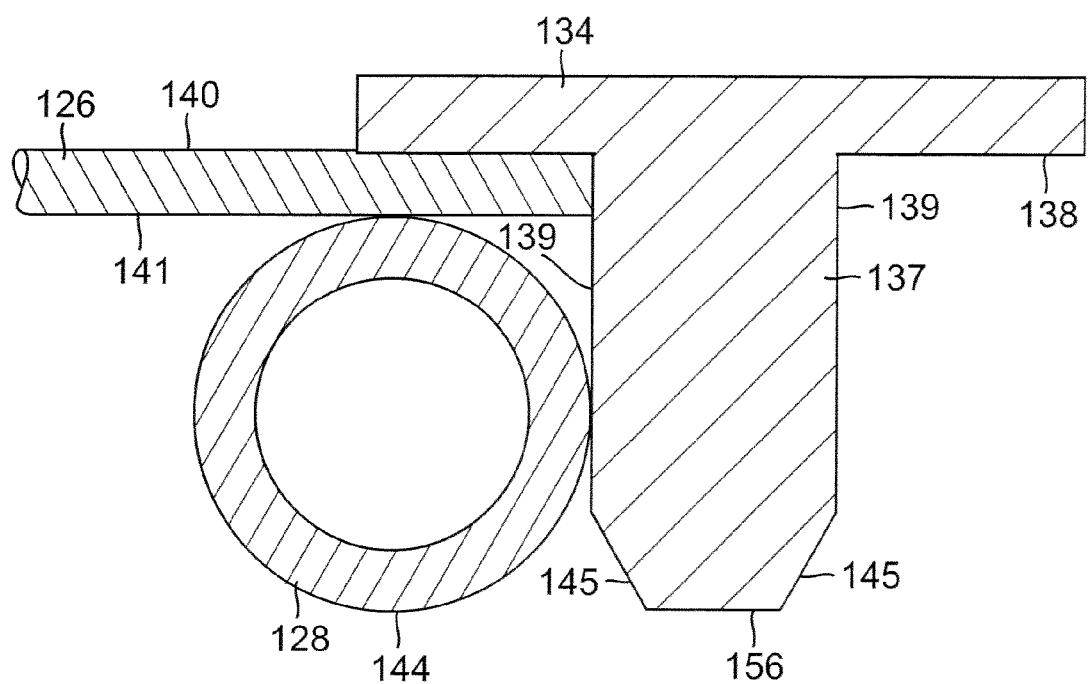
FIG. 6 is a cross-sectional schematic partial view of a seal ring, contact ring and spring contact element according to aspects of the current invention.

In accordance with aspects of the present invention, two sub-classes of seal rings 124 are incorporated including an end seal ring 132 and an intermediate seal ring 134. The end seal ring 132 comprises a single internal shoulder 138 for receiving an adjacent exterior wall surface 140 of a ring contact 126 or otherwise. With reference now also to FIG. 6, each intermediate seal ring 134 comprises an annulus 137, which resembles an inwardly protruding flange defining two interior side walls 139 defining a lip 156 therebetween, and two internal shoulders 138 for receiving an adjacent exterior wall surface 140, which could be that of two different ring contacts 126 or otherwise, such as one ring contact 126 and a holding ring 130. The lip 156 defines an internal bore having an internal diameter adapted to receive a lead cable, as further discussed below. In an alternative embodiment, an intermediate seal ring 134 can be used in place of an end seal ring 132 without deviating from the spirit and scope of the present invention.

Figure 9:
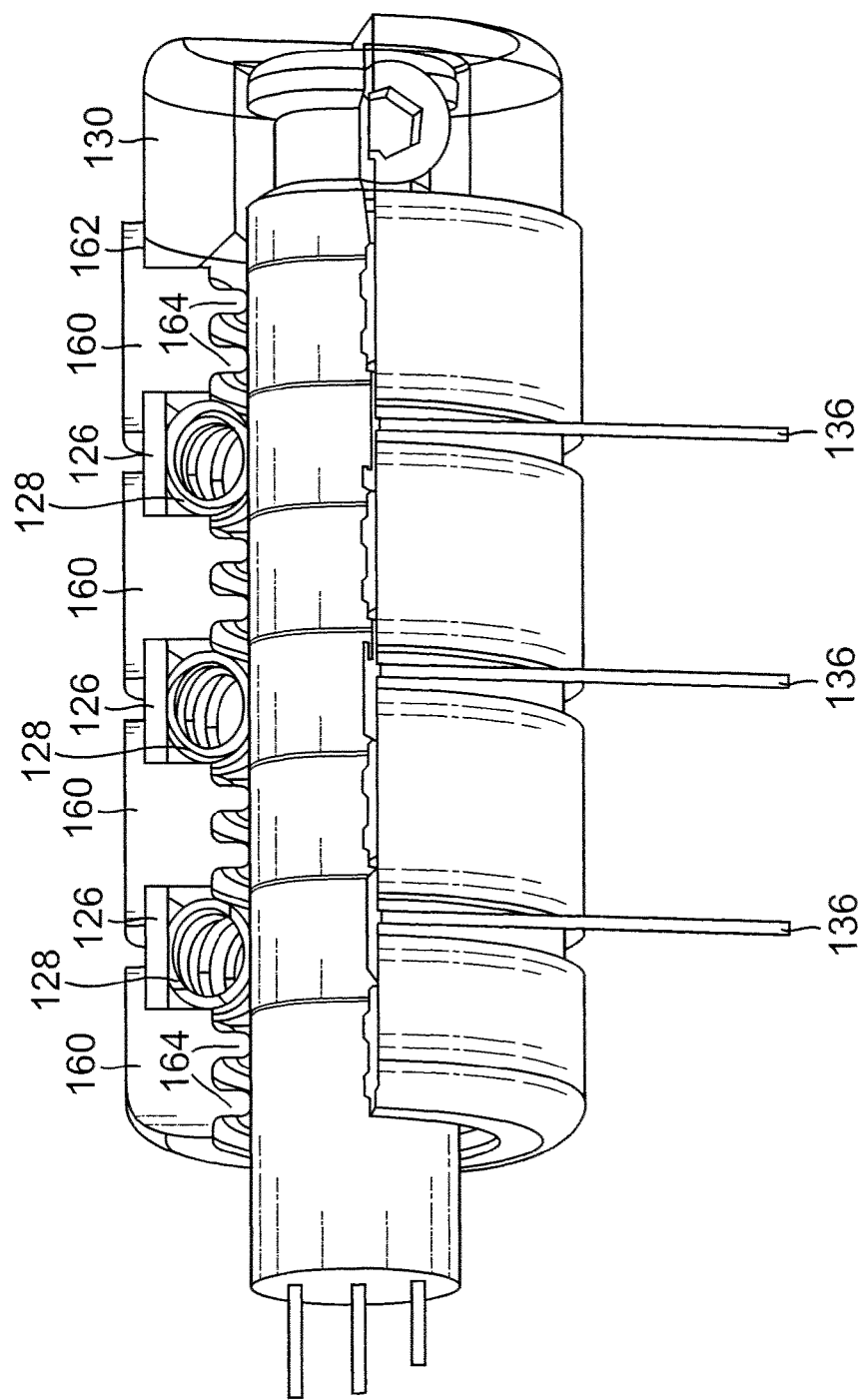
FIG. 9 is an isometric cut-away view of an alternate embodiment of a connector assembly in an assembled state including seal rings having double lip seal configuration.

In one exemplary embodiment of the present invention, a surface of the annulus or flange 137 has two beveled or tapered edges 145 configured to facilitate assembly of the connector apparatus or insertion of a lead cable. As is readily apparent to a person of ordinary skill in the art, the tapered surfaces redirect an alignment pin or a lead cable through the internal bore of the seal ring when the same come in contact therewith. In another exemplary embodiment, a seal ring 160 (FIG. 9) has an annulus or inwardly protruding flange 162 having a double sealing lip configuration 164 on its interior bore surface. The alternative seal ring comprises four tapered or beveled edges defining two lips. During use, the double sealing lip configuration 164 enhances the sealing ability of the seal ring against the lead cable. One skilled in the art will appreciate that other annulus shapes and lip shapes are possible without deviating from the scope or spirit of the invention. Additionally, although a single flange or annulus is described, multiple flanges spaced from each other may also be incorporated.

Figure 7:
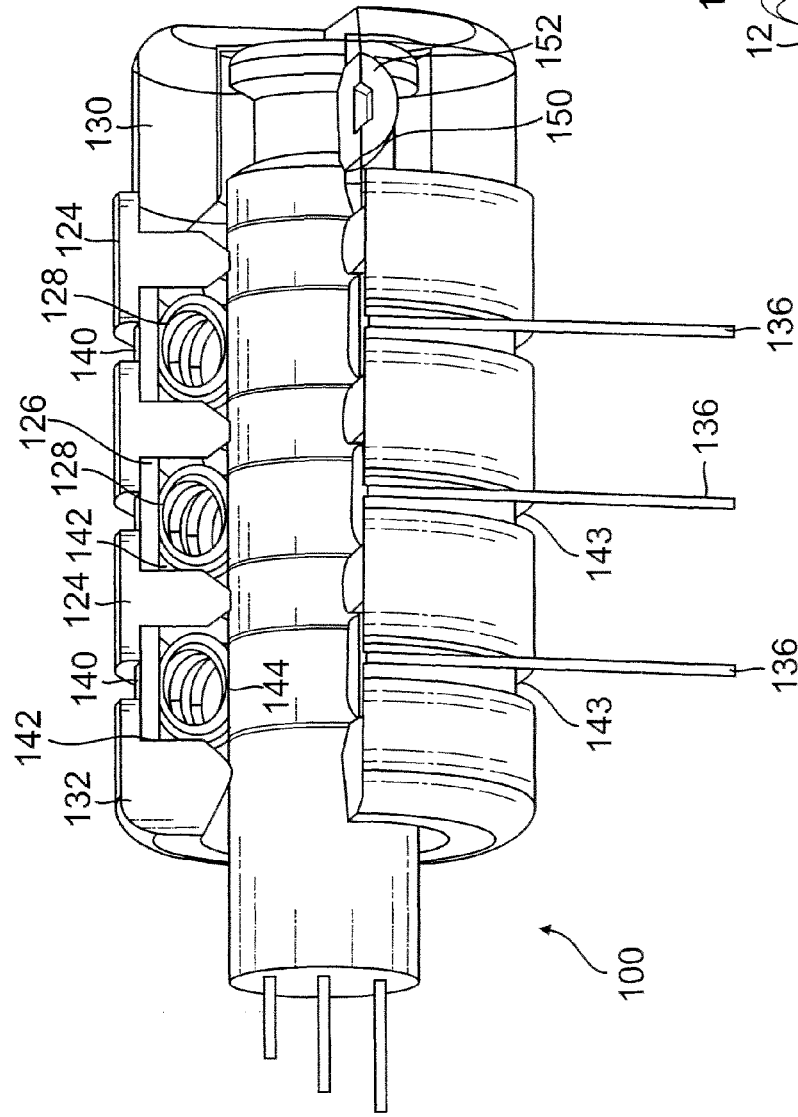
FIG. 7 is an isometric cut-away view of the connector assembly of FIG. 5 in an assembled state with a medical lead cable disposed in the connector bore.

With reference now also to FIG. 7, when two adjacent seal rings 124 engage the exterior wall surface 140 of a common ring contact element 128 such that the ring contact element abuts the interior side walls 139 and the interior shoulder 138 of the seal rings 124, a spring chamber 142 is formed for accommodating a spring contact element 128. The spring contact element 128, which is preferably a radial or axial canted coil spring commercially available along with the seals from Bal Seal Engineering of Foothill Ranch, Calif., is sized so that it is positioned by the groove along its two axial ends and establishes contact along its outer and inner radial circumference. Its internal diameter 144 is preferably smaller than an internal diameter defined by the interior bore 156 of the seal ring 124, which is slightly smaller than the outer diameter of the proximal end 13 of the lead cable 12. In other words, when the proximal end 13 of the lead cable 12 is inserted into the common bore, the lead cable has a slight interference fit with the plurality of seal rings 124 and the canted coil springs. The seal rings 124 are also in interference fit with the adjacent external wall surfaces 140 of the ring contacts 128 along their respective internal shoulders 138 to ensure proper sealing between the various components. In one exemplary embodiment, the ring contacts 128 each comprises a width that may be greater than a combined depth of two adjacent internal shoulders 138 of two adjacent seal rings 124, thus defining a gap 143 between the seal rings 124. The gap 143 allows one end of a lead 136 to be connected directly to the ring contact element 128.

The spring contacts 128 are similarly sized so that each is deflected by the lead cable 12 to about 5% and up to about 50% of its total radial deflection with up to about 40% being more preferred. This deflection range ensures a sufficient spring contact force is generated between the contract rings 126 and the electric terminals 16 on the lead cable 12 for transferring electric signals between the two.

Referring again to FIG. 5, in one exemplary embodiment, the ring contacts 126 are each generally cylindrical in configuration. More preferably, each ring contact 126 has a generally constant inner diameter and outer diameter with two square ends, with normal manufacturing tolerance being acceptable. In other words, the ring contacts 126 do not have machined or formed grooves for forming spring chambers therein for accommodating the spring contact elements 128. The ring contacts 126 have a simple profile, which makes manufacturing the rings and assembling the spring contacts 128 therein easier and therefore more cost effective. The spring chambers 142 are formed instead by a combination of interior side walls 139 of adjacent seal rings 124 and the interior wall surface 141 of the ring contact element 126. While FIG. 5 is an exemplary design, alternative ring contact internal geometries are possible, similar to those described above.

In the embodiment shown in FIG. 5, the holding ring 130 functions as an end cap and has an end wall 147 and an exterior wall surface 148 for mating engagement with the interior shoulder 138 of a seal ring 134. The end caps also function to properly compress a stack of connectors such that the assembly can be over-molded without leakage of the over-molding material into the assembly. As is also shown in FIG. 7, a threaded bore 150 for receiving a set screw 152 is incorporated in the holding ring 130 to more securely fix the lead cable 12 to the connector 100 assembly. Alternatively, an end holding ring (not shown) may be incorporated at the distal most end of the connector assembly for providing the locking function on the lead cable 12.

Referring again to FIG. 7, the seal rings 124 of the present embodiment, except for the end seal ring 132, are each symmetrical about a centerline drawn perpendicular to the axis defined by the lead cable 12 and through the center of the seal ring. However, non-symmetry or other configurations are possible so long as a spring chamber for accommodating a spring contact is formed at least in part by engaging the ring contact 126 with two adjacent seal rings 124. Furthermore, while the seal rings 124 of the present embodiment are shown each comprising an internal projection for sealing against the lead cable 12, two or more projections may be incorporated without deviating from the spirit and scope of the present invention. Still furthermore, part of the seal ring that projects over the external surface of a ring contact can be made separately. In other words, a seal ring may be made by co-molding or over-molding two separate components.

Figure 8:
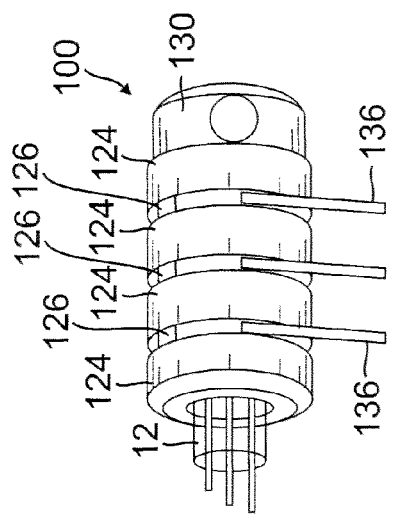
FIG. 8 is an isometric view of the connector assembly of FIG. 7.

Additionally, in accordance with one aspect of the present invention, a method is provided for assembling a plurality of components to form a connector assembly as described above. Following assembly of the various components to form the connector assembly 10 shown in FIG. 7, the connector assembly is encased inside an implantable elastomer or polymer layer, as previously discussed. FIG. 8 is a fully assembled view of the connector assembly 100 of FIGS. 5 and 7 with the medical lead cable 12 disposed inside the common bore.

Thus, aspects of the present invention include steps for assembling a medical connector stack comprising the steps of sliding a conductive ring element over a shoulder of each of two adjacent seal elements (FIGS. 1-2) or under a shoulder of each of two adjacent seal elements (FIGS. 5, 9, and 10) to form a ring groove comprising a conductive bottom wall surface and two non-conductive side wall surfaces; and placing a canted coil spring into the ring groove. A further aspect of the present invention is a provision for forming an implantable medical connector stack comprising the steps of providing an assembly pin, placing a dielectric seal element onto the assembly pin, placing a conductive ring element onto the assembly pin, placing a canted coil spring onto the assembly pin and inside the conductive ring element; placing a second dielectric seal element onto the assembly; and sliding the conductive ring element into engagement with the two dielectric seal elements to form a ring groove for retaining the canted coil spring. This method lends itself to ease of assembly of a connector stack including automated assembly.

FIG. 10 is a sectional assembled side view of another connector assembly or stack 180 provided in accordance with aspects of the present invention. Like previously discussed connector assemblies, the present embodiment incorporates similar basic components, namely two end seals 182, a plurality of ring contact elements 184, a plurality of seal rings 186, and a plurality of canted coil springs 188, which may be an annular radial canted coil spring or an annular axial canted coil spring. The assembled components have a common bore for receiving a medical lead cable 12.

While the number of end seals 182 per connector assembly 180 are generally two, the number of ring contact elements 184, seal rings 186, and canted coil springs 188 may vary depending on the particular application, e.g., unipolar, bipolar, or multi-polar application. As shown, the connector assembly 180 is a multi-polar connector assembly having seven conductive points for electrically coupling with a seven electrode medical lead cable 12.

In one exemplary embodiment, the end seals 182 each incorporates two projections or annular rings 190 for sealing against a lead insulator to prevent fluid from seeping into the common bore. A square shoulder 192 is incorporated to abut against an adjacent contact ring element 184 along an axial direction and compresses over the adjacent contact ring in a radial direction, in an interference fit. The shoulder 192 has a sufficient depth to receive the adjacent ring contact element 184 yet not too deep so as to provide a gap 194 with and adjacent seal ring exteriorly so that contact between the ring contact element and a contact conductor 36 could be made. The ends seals 182 and the seal rings 186 are preferably made from a medical grade polymer or elastomer, such as silicone. Thus, as such material is flexible and resilient, a range of interference fit is possible which provides for manufacturing flexibility in terms of tolerance and accuracy.

With reference now to FIG. 10A in addition to FIG. 10, an enlarged simple cross-sectional side view of a contact ring element 184 engaged to a seal ring 186 is shown. In one exemplary embodiment, the contact ring element 184 comprises a cavity 196 for accommodating the canted coil spring 188. As shown, the cavity 196 is defined by a cavity base 200 that represents an obtuse angle and a side wall 198. For illustration purposes, the side of the contact ring element with the side wall 198 may be referred to as the first side or closed side 199 and the other side without the side wall may be referred to as the second side or opened side 201. The single-sided cavity 194 is easier to manufacture than a similar cavity with two identical or similar side walls. Additionally, installation of the coil spring 188 into the cavity from the opened side 201 is easier and requires no special tools.

To engage the ring contact element 184 to the adjacent seal ring 186, an axial projection 202 is incorporated on the opened side 201, which is configured to project into a groove 204 on the seal ring 186, in an interference fit arrangement. The contact ring is made from a conductive material and in an exemplary embodiment is made from a steel material, such as medical grade stainless steel, titanium, noble metals such as platinum or conventional implantable grade materials with noble metal coatings, such as platinum over stainless steel. The groove 204 is formed on a first wall side 206 of the seal ring 186, which partially shields or covers the coil spring 188 on the opened side 201 of the contact ring 184. In one exemplary embodiment, a clearance or small gap is provided between the first wall side 206 and the spring 188 such that the spring does not abut or contact the first wall side during use. However, after insertion of a lead cable 12 and during removal of the lead cable 12, the spring may shift and contacts the first wall side 206. Still alternatively, the spring could be sized so that it contacts the first wall side during normal use.

Like the end seals 182, the seal ring 186 incorporates an annular projection 190 for forming a seal against a lead insulator on a medical lead cable, similar to previously discussed embodiments. Although a single annular projection 190 is shown, two or more projections may be incorporated without deviating from the spirit and scope of the present invention. Also like the end seals, a square shoulder 192 comprising a second wall side 208 and an axially extending wall 210 are incorporated to receive a closed side 199 of an adjacent contact element (shown in FIGS. 10 and 11 but not in FIG. 10A). As the seal ring 186 is circumferential, the axially extending wall 210 is configured to compress a contact ring in an interference fit arrangement to provide a fluid tight seal along the interface of the two components.

With reference again to FIG. 10, a holding or locking ring 212 is incorporated adjacent an end seal 182. More particularly, as the end seal 182 adjacent the holding ring 212 acts as an entrance to the common bore of the connector assembly 180, which is an opening for insertion by the medical lead cable 12, the holding ring 212 may be thought of as a front end locking ring. This locking ring location is configured for use with a lead cable that has a locking groove 213 located distally of the last contact ring 186.

In one exemplary embodiment, the locking ring 212 may be made from the same material as the ring contact element. Alternatively, it could be made from an implantable grade non-conductive rigid plastic material, such as from PolyEtherEtherKetone (PEEK). The ring 212 has a threaded bore 50 and a set screw 52 for more permanently securing the lead cable to the connector assembly 180.

The components of the connector assembly 180 may be assembled in the manner and fashion as previously discussed for other connector assemblies. Once assembled, the contact ring elements 184 are each compressed along a closed side 199 by a shoulder of one seal ring and compressed along an opened side 201 by a tongue and groove arrangement to seal the contact ring exteriorly from moisture or fluid. The assembled connector assembly 180 is then subject to an overmolding process or is inserted into a pre-formed header to retain the assembled components in an assembled state.

Figure 12:
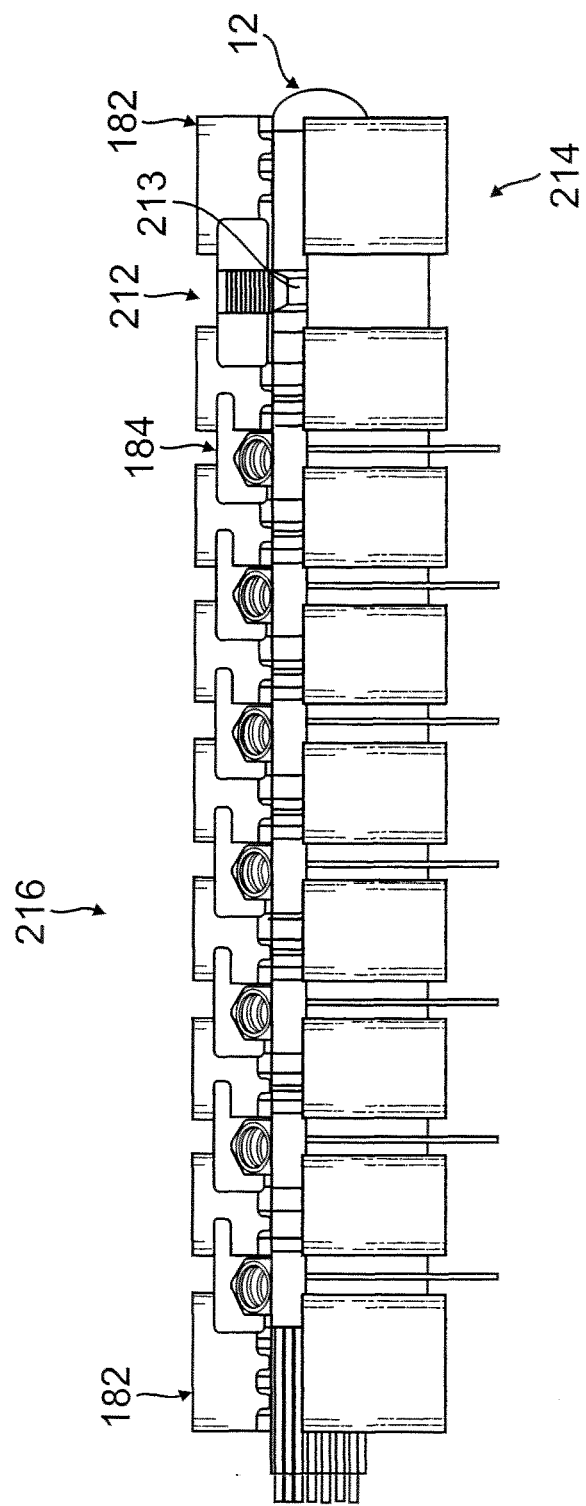
FIG. 12 is an alternative configuration of the connector assembly of FIGS. 10-11.

FIG. 12 is a sectional assembled view of the connector assembly of FIGS. 10-11 in a different configuration. In the present embodiment, the holding ring 212 has been located to the back side 214 of the connector assembly 216, which is away from the front side or entrance 218 to the connector assembly for receiving the lead cable 12 into the common bore. This configuration is used for mounting a medical lead cable in which the locking groove on the lead cable is located proximally of the first contact ring element 184.

Figure 13:
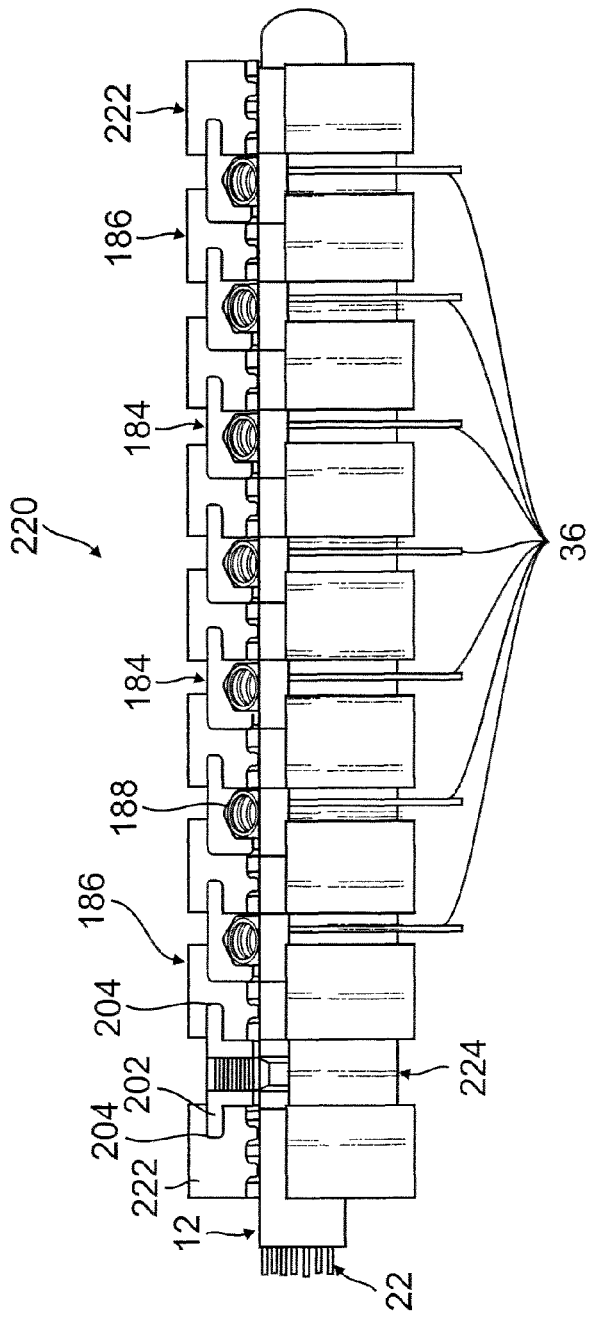
FIGS. 13-15 show yet another alternative connector assembly in accordance with aspects of the present invention.

FIG. 13 is a sectional assembled view of yet another connector assembly 220 provided in accordance with aspects of the present invention. Like the other connector assemblies, the present connector assembly 220 may be used with a can as an IMD either in a single connector assembly application (similar to that shown in FIG. 4) or a multi-connector assembly application in which two or more connector assemblies or stacks are located either in a side-by-side configuration or one on top of the other.

In the embodiment shown, the connector assembly 220 incorporates two end seals 222, a plurality of sealing rings 186, a plurality of ring contact elements 184, and a plurality of canted coil spring 188 interconnected with a common bore for receiving a medical lead cable 12, which has a plurality of electrode leads 22. The present embodiment is similar to the connector assemblies shown in FIGS. 10-12 with the exception of the two ends seals 222. Instead of a square shoulder, the two end seals 222 each incorporates a groove 204 for receiving an axial projection 202 of an adjacent ring contact element 184 or, if viewed from the perspective of an opposing end seal 222, an axial projection 202 of a locking ring 224. The locking ring 224 (FIGS. 13-14) has been modified to incorporate two opposing axial projections 202, one for engaging a groove 204 of the end seal 222 and the other for engaging the groove 204 of a seal ring 186.

Figure 14:
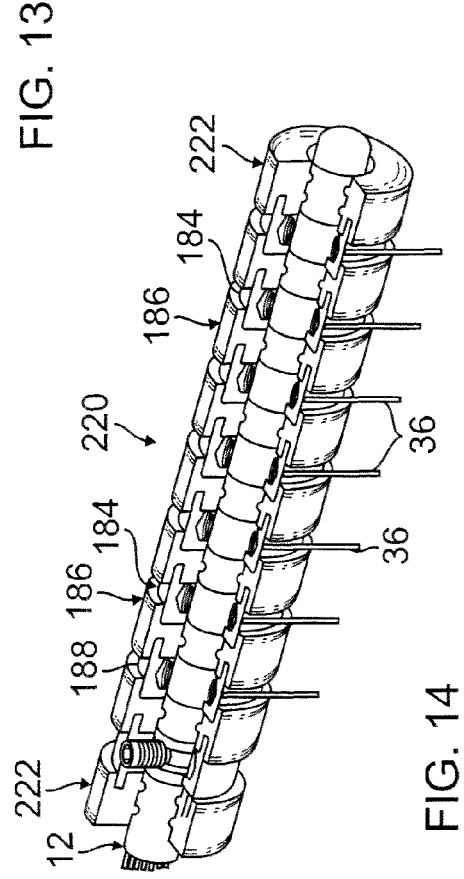
Figure 15:
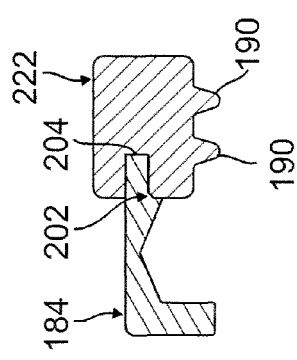

FIG. 15 is a simple enlarged cross-sectional view of a ring contact element 184 of FIGS. 13 and 14 having its projection 202 inserted into a groove 204 of an end seal 222.

Figure 16:
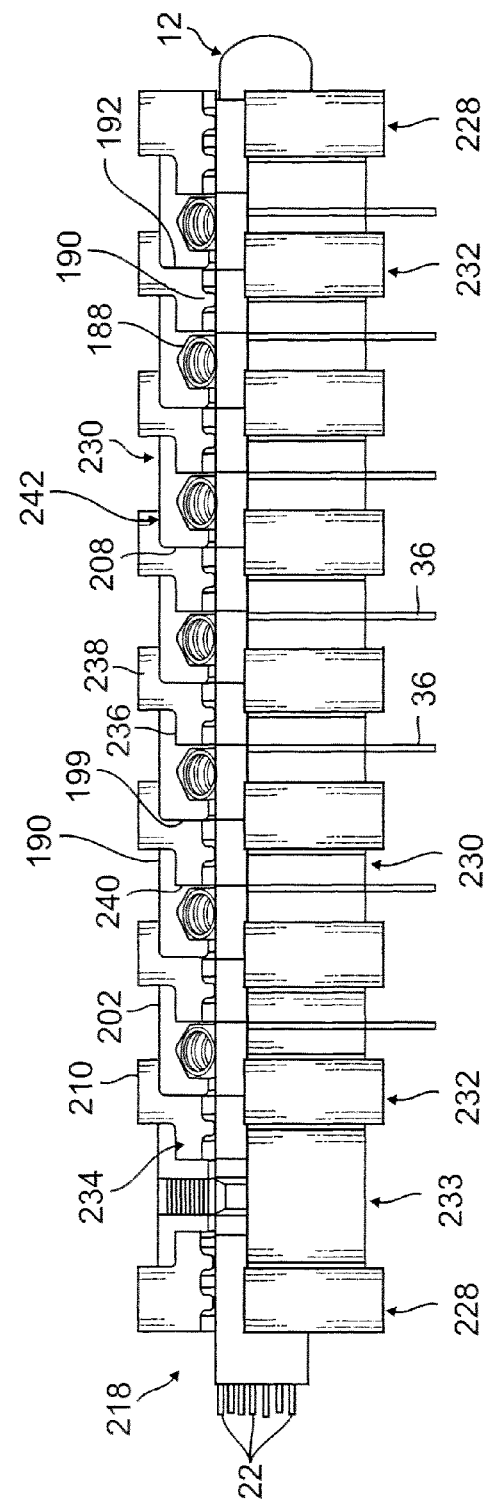
FIGS. 16-17 show still yet another alternative connector assembly in accordance with aspects of the present invention.

FIG. 16 is a sectional assembled view of yet another connector assembly 226 provided in accordance with aspects of the present invention. In one exemplary embodiment, the connector assembly 226 comprises two ends seals 228, a plurality of ring contact elements 230, a plurality of seal rings 232, a plurality of canted coil springs 188, and a locking ring 233. As shown, the ring contact elements 230 are similar to those shown and discussed with reference to FIGS. 10-15 and the locking ring 233 is similar to that shown and discussed with reference to FIG. 13.

Because the seal rings in the present embodiment are identical, only a single seal ring will be discussed. In the present embodiment, the seal ring 232 is configured to mate with two adjacent contact rings, or one contact ring and one locking ring, in an over-under configuration. The seal ring 232 incorporates a reduced outside diameter (OD) section 234 for projecting under an axially extending wall section 202 of a contact ring element 230. The reduced OD section 234 comprises a first surface 236 for an under compression fit arrangement with a contact ring element, as further discussed below, and a second surface 238 at an angle to the first surface 236 for axially limiting the depth of insertion of the reduced OD section 234 into the contact ring element. In an alternative embodiment, the insertion depth is instead controlled by the surface of the partial side wall 240 adjacent the obtuse angled wall of the contact ring element abutting an axial end edge of the reduced OD section.

Once assembled, the axial projection 202 on the contact ring element 230 is configured to compress the reduced OD section 234 to provide a moisture and/or fluid tight seal around the exterior surface of the reduced OD section. As is readily apparent to a person of ordinary skill in the art, chamfered edges are preferably incorporated at various corners for easy insertion and assembly between the different components.

In the embodiment shown, the seal ring 232 incorporates a compression fit section 242 for an over fit arrangement with an adjacent contact ring element. In one particular application, the over compression fit section 242 comprises an axially extending wall 210 and a second wall side 208 that define a square shoulder 192, similar to the square shoulder incorporated in the seal ring 186 shown and discussed with reference to FIG. 10A. The over compression fit section 242 is configured to receive a closed side 199 of an adjacent contact ring element and compresses that section to form a moisture and/or fluid tight seal. Interiorly, the seal ring incorporates an annular projection 190 for forming a interference fit over a corresponding lead insulator section of the medical lead cable 12.

Figure 17:
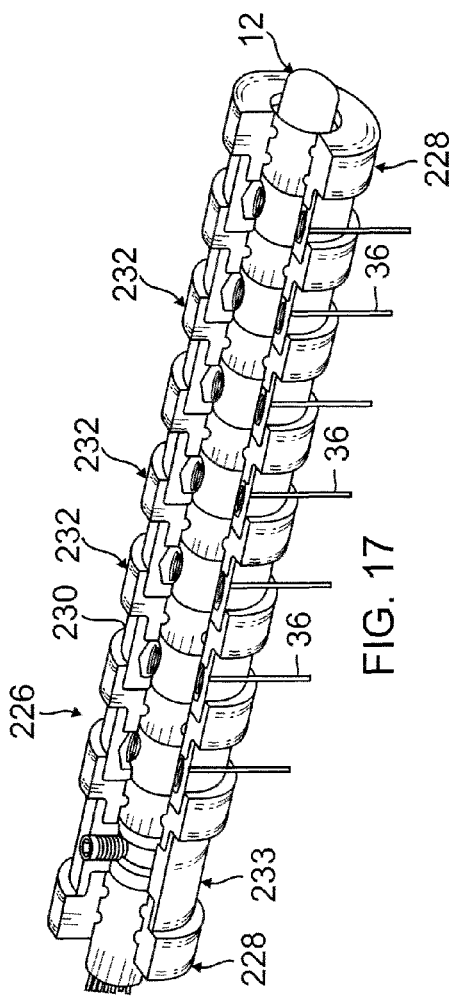

FIG. 17 is an isometric view of the connector assembly 226 of FIG. 16. As shown, the connector assembly is configured to receive a lead cable 12 with seven-electrode leads 22. However, the connector assembly may be made with fewer or more components to accommodate a lead cable with a different number of electrode leads. Additionally, while the locking ring 233 is shown located at the front end 218 of the connector assembly, near the opening to the common bore, the locking ring can readily be placed near the back side to accommodate a lead cable with a proximally located locking groove.

Figure 18:
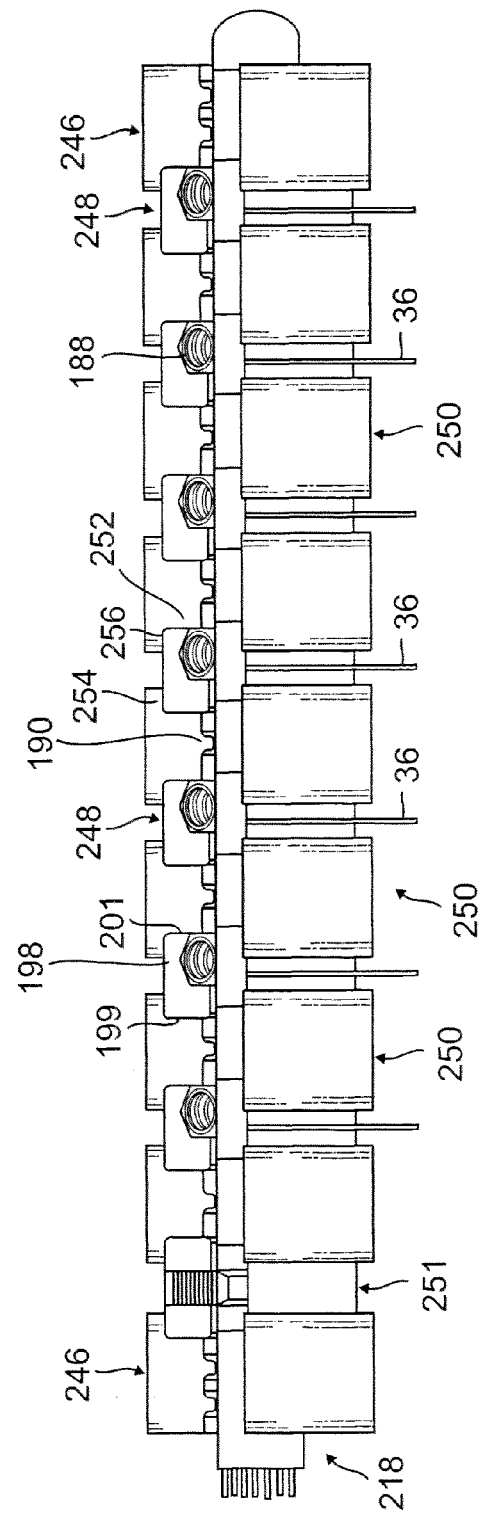
FIGS. 18-19 show yet another alternative connector assembly in accordance with aspects of the present invention.

FIG. 18 is yet another connector assembly 244 provided in accordance with aspects of the present invention. The connector assembly comprises two end seals 246, a plurality of ring contact elements 248, a plurality of seal rings 250, a plurality of canted coil springs 188, and a holding ring or locking ring 251 near the front end or opening of the connector assembly. In the embodiment shown, the two end seals 246 are similar to the end seals 182 shown and discussed above with reference to FIGS. 10 and 11. The contact rings 248 are also similar to the ring contact elements 184 shown and discussed with reference to FIGS. 10 and 10A with one exception, the present ring contact elements 248 do not incorporate an axial wall section 202 for engaging a groove of an adjacent seal ring. Instead, the opened side 201 of each contact ring 248 has a generally flat but shallower wall than the wall 198 of the closed side 199 of the contact element. Said differently, the opened side 201 is defined by a line drawn radially outwardly from a distal tip of the obtuse angled wall of the cavity. This opened side 201 is configured to be inserted into an adjacent seal ring 250, as further discussed below.

In one exemplary embodiment, the seal rings 250 of the present embodiment are generally symmetrical about a centerline drawn through the annular projection 190 of each seal ring in a radial direction. The seal rings 250 each incorporates an axially facing wall side 252 and a radially facing wall side 254 for defining a shoulder 256. The shoulder 256 is adapted to receive either the opened side 201 or the closed side 199 of an adjacent contact ring element. More specifically, when an end of a contact ring element is received against the shoulder 256, a moisture and/or fluid tight seal is formed exteriorly of the ring contact element.

Figure 19:
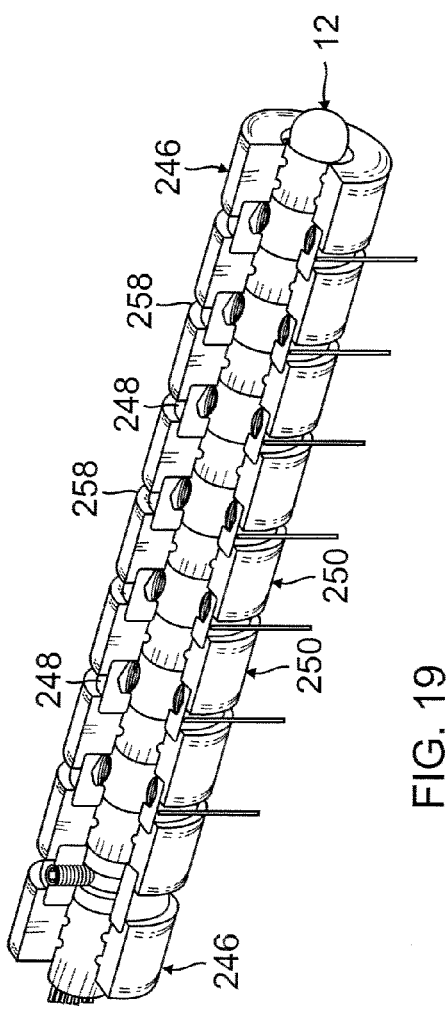

As shown in FIG. 19, a gap 258 is provided between two adjacent seal rings 250. As is readily apparent to a person of ordinary skill in the art, the width of the gap 258 may be controlled or regulated by the depth of the shoulder of the two adjacent seal rings. The gap is provided to enable a contact conductor 36 from a can or sealed housing of a IMD to be welded to a corresponding contact ring element. Also as previously discussed, the number of ring contact elements, canted coil springs, and seal rings incorporated in the connector assembly 244 may vary depending on the application, which in turn depends on the type of medical lead cable the connector assembly 244 is configured to receive. Still furthermore, the connector assembly 244 may be installed to a can by itself or with one or more other connector assemblies arranged either side-by-side or on top of one another.

Thus, in accordance with aspects of the present invention, a method for forming a connector stack is provided wherein a ring groove is formed by a ring contact element having one conductive side wall and one non-conductive side wall formed by an adjacent dielectric seal element. A further aspect of the present invention is a provision for forming an implantable medical connector stack comprising the steps of providing an assembly pin, placing a dielectric seal element onto the assembly pin, placing a conductive ring element onto the assembly pin, said conductive ring element comprising a closed side comprising a side wall and an opened side, placing a canted coil spring onto the assembly pin and inside the conductive ring element through the opened side; placing a second dielectric seal element onto the assembly; and sliding the conductive ring element into engagement with the two dielectric seal elements to form a ring groove comprising one side wall of a conductive material and one side wall of a non-conductive material for retaining the canted coil spring.

Figure 20:
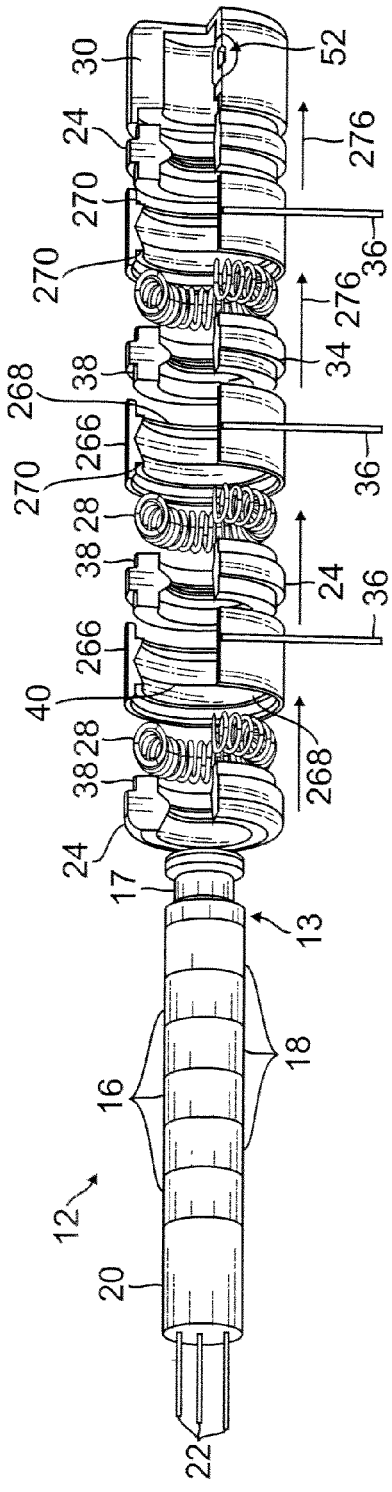
FIG. 20-21 show yet another alternative connector assembly in accordance with aspects of the present invention.

FIG. 20 is an exploded cut-away perspective view of yet another implantable connector assembly or stack 264 provided in accordance with aspects of the present invention. In one embodiment, the connector stack 264 comprises, from right to left of FIG. 20, a holding ring 30, and several sets of: a seal ring element 24, a ring contact element 266, and a canted coil spring 28. The assembly has one end seal ring 24 located at the distal end 54 of the connector stack 264. The number of sets depend on the particular application of the connector stack. In the present embodiment, the stack is configured for use with a three node lead cable 12 and therefore incorporates three ring contact elements 266 and three canted coil springs 28. However, the embodiment and the invention is not so limited and can vary depending on the particular application. In one embodiment, the holding ring 30 and the seal ring elements 24 are the same as the holding ring and seal ring elements of FIGS. 1-4. Accordingly, only the features of the ring contact elements 266 will be discussed.

The ring contact elements 266 each has two axial end openings 268 and an internal shoulder 270 at each opening. The internal shoulders 270 are each defined by a lip 272, which is located at an outer edge of a V-groove 274. The ring contact elements 266 may be machined from a tubular material or cast molded using conventional molding techniques. The V-groove 274 is configured to axially set and retain a canted coil spring within the bore 40 of the ring contact element and provide a two-point contact with the spring.

The stack 264 may be assembled by inserting the various components in the direction of the insertion arrow 276, starting with the holding ring 30. In one embodiment, an assembly rod or installation rod (not shown), similar in diameter and shape as the medical lad cable 12, is first attached to the holding ring 30 by tightening the set screw 52 against a groove located on the assembly rod. The various components are then slid onto the rod and pushed in the direction of the insertion arrow 276. In other embodiments, the various components are simply inserted in the direction of the insertion arrow without an assembly rod. Three contact conductors 36 are shown each attached to a contact ring element 266, such as by laser welding. In practice, this usually only occurs after the assembled stack 264 is placed into a header of an implantable medical device (IMD), as further discussed below.

Figure 21:
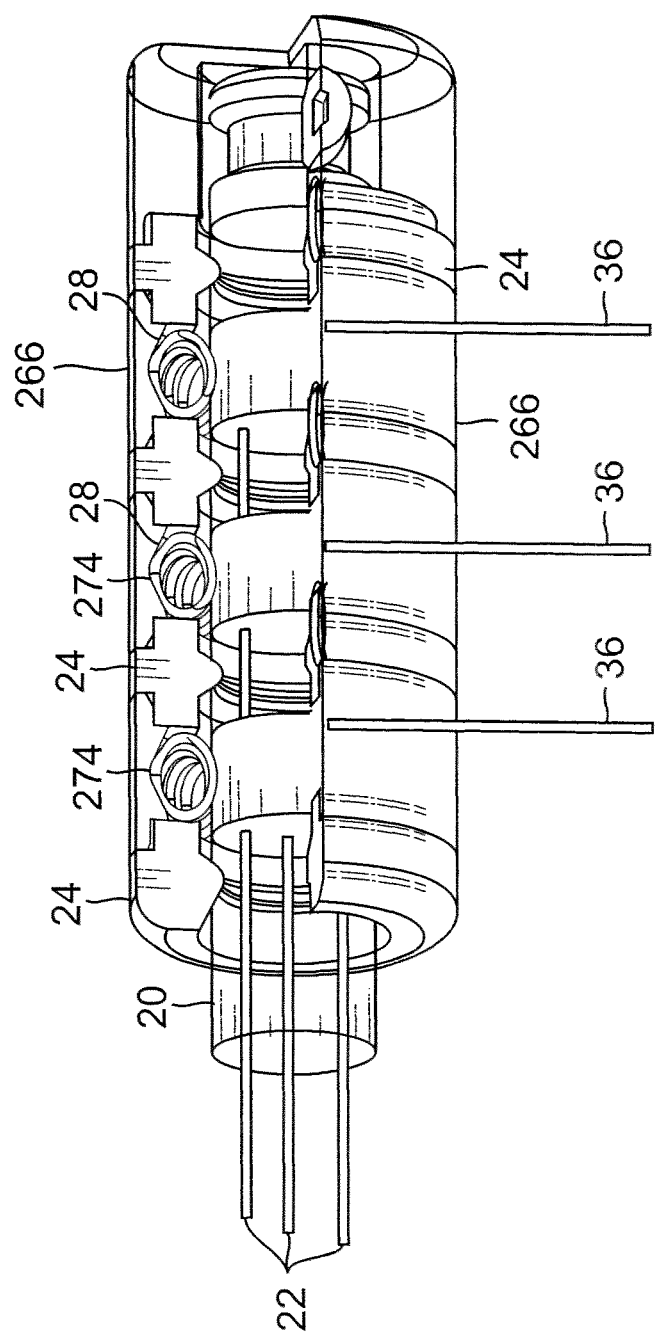

FIG. 21 is a cut-away perspective view of the stack 264 of FIG. 20 fully assembled and having a medical lead cable 12 inserted into the common bore. Once the lead cable 12 is inserted, it is secured by tightening down on the set screw 52, which clamps down on the groove 17 located at the proximal end 13 of the lead cable 12 to prevent the lead cable from axially backing out of the bore. As shown, the electrical terminals 16 on the lead cable 12 align with and contact a corresponding canted coil spring 28. In practice, this allows electrical signals sent through the contact conductors 36 to pass through the ring contact elements 266, through the canted coil springs 28, and to the electrical terminals 16, which then communicate with corresponding electrode leads 22 located inside the medical lead cable 12.

Figure 22:
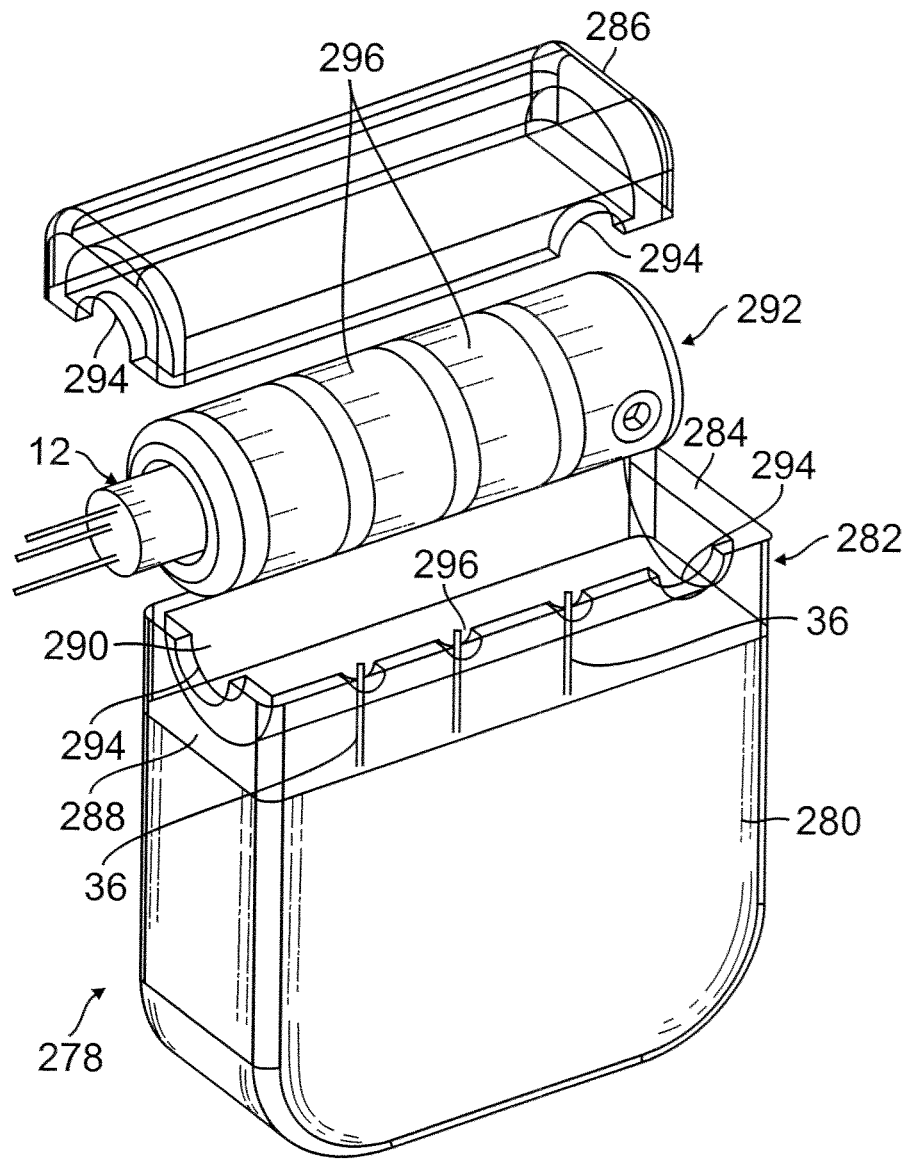
FIG. 22-23 are schematic views of a connector stack being placed in a pre-formed header comprising a cavity for accommodating the stack.

FIG. 22 is an exploded perspective view of an IMD 278, which may be an implantable pulse generator (IPG), which has a can 280 and a header 282, shown in an exploded view along a parting line 284. The header 282 comprises an upper header section 286 and a lower header section 288, both of which having a cavity 290 that together form a tight fitting space for accommodating a medical connector stack 292. The medical connector stack 292 in turn receives a medical lead cable 12. In one embodiment, the connector stack 292 may embody any of the stacks described elsewhere herein, such as the stacks of FIGS. 1-3, 5, 9, 10, 12, 13, 16, 18, and 20.

In one embodiment, the upper and lower header sections 286, 288 also incorporate cut-outs 294 for providing access to the opening of the common bore and to the set screw. The lower header section 288, and optionally the upper header section 290, also incorporates cut-outs 296 for accessing the contact conductors 36. The contact conductors 36 project through one or more feed through terminals that pass through the hermetically sealed housing or can 280 to contact the contact rings 296 as the stack is placed inside the header, as shown in FIG. 23.

Figure 23:
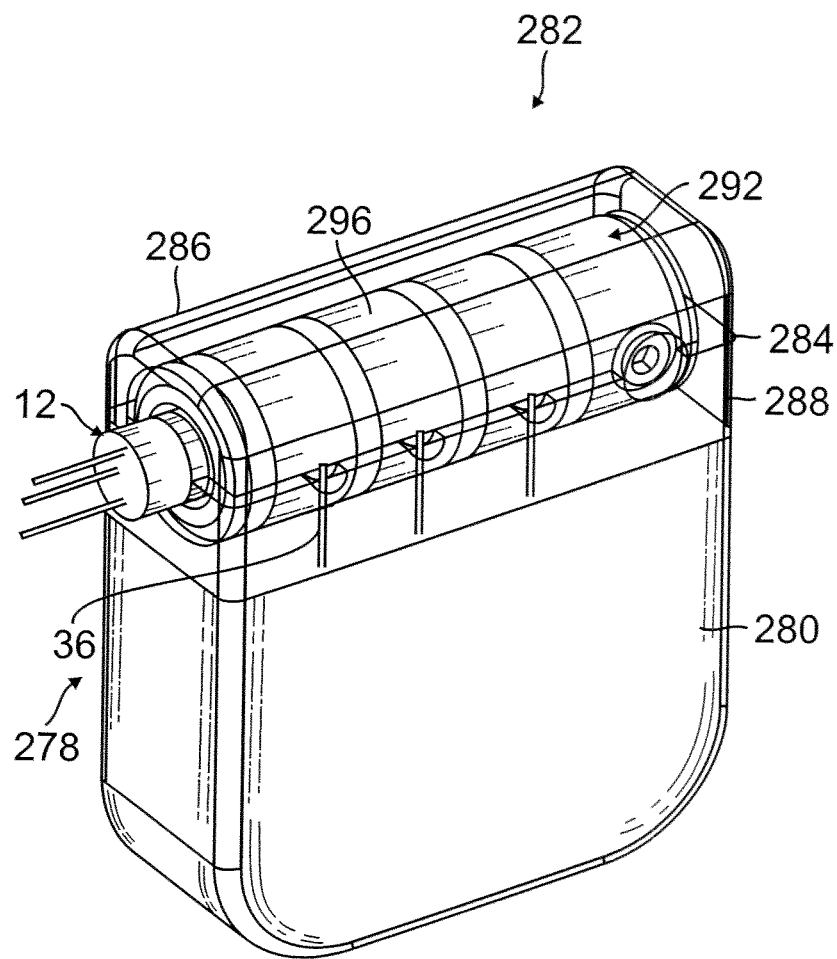

FIG. 23 shows the connector stack 292 situated inside the header 292 and the two header sections 286, 288 attached to one another along the parting line 284. In one embodiment, the two header sections may be glued or bonded together using any known prior art methods. Either before or after the two header sections are attached to one another, the contact conductors 36 are welded to corresponding ring contact elements 296. The lead cable 12 is then inserted into the common bore and is secured to the stack by tightening down on the set screw. The cut-outs 294 for the contact conductors 294 and the set screw 294 are then back-filled using implantable grade polymer or elastomer material.

Although limited preferred embodiments and methods for making and using connector assemblies provided in accordance with aspects of the present invention have been specifically described and illustrated, many modifications and variations will be apparent to those skilled in the art. For example, various material changes may be used, incorporating different mechanical engagement means to attach the various components to one another, making use of two or more different materials or composites, making a sealing ring from multiple pieces rather than a singularly molded piece, etc. Moreover, the connector assemblies provided herein may be used in conjunction with an Extension, which is used for testing implanted electrode terminals or implanted activator units so that programs or controls used to manipulate the implanted electrode terminals and the like can be programmed for the IMD. Still alternatively, the connector assembly may be used for any device that requires an in-line connection in which multiple conductive sources are to be relayed between a source generator and a source receiver, whether that device is configured for implanting or otherwise. Also. while certain connector stacks are shown and disclosed for use with a three node or three electrode terminal lead cable, the number of seal elements, ring contact elements, and canted coil springs are not limited to the embodiments as shown and can include more or less depending on the particular application. Accordingly, it is to be understood that the connector assemblies constructed according to principles of this invention may be embodied in other than as specifically described herein. The invention is also defined in the following claims.

What is claimed is:

1. An implantable medical connector stack having easy to install ring grooves for receiving contact springs comprising:
    a first seal element made of a dielectric material comprising an annulus comprising a projection; said annulus comprising a generally planar wall surface;
    a conductive ring contact element comprising an interior wall surface adjacent at least one axial opening;
    a second seal element made of a dielectric material comprising an annulus comprising a projection;
    a canted coil spring;
    wherein the conductive ring contact element is engaged to the first seal element and the second seal element and a ring groove is formed by a bottom wall of the conductive ring contact element and two side walls formed from one each of the first and second seal elements; and
    wherein the generally planar wall surface of the first seal element forms a dielectric side wall of the ring groove that together with the interior wall surface of the conductive ring contact element define a physical stop for retaining the canted coil spring inside the ring groove, and a portion of at least one of the seal elements projects into the conductive ring contact element.

2. The implantable medical connector stack of claim 1, further comprising a bore that is common to the conductive ring contact element and the first and second seal elements.

3. The implantable medical connector stack of claim 1, wherein the conductive ring contact element engages the first seal element and the second seal element by projecting over a shoulder on each of the first seal element and the second seal element.

4. The implantable medical connector stack of claim 1, wherein the conductive ring contact element engages the first seal element and the second seal element by projecting under a shoulder on each of the first seal element and the second seal element.

5. The implantable medical connector stack of claim 1, wherein the annulus of the first seal element comprises a second projection.

6. The implantable medical connector stack of claim 1, wherein the stack is positioned inside an elastomeric or polymer header.

7. The implantable medical connector stack of claim 6, wherein the header is attached to a sealed housing of an implantable medical device.

8. The implantable medical connector stack of claim 1, wherein the conductive ring contact element comprises a bottom wall having a V-shape configuration.

9. The implantable medical connector stack of claim 1, wherein the conductive ring contact element comprises an axially extending wall that projects into a groove of the first seal element and the generally planar wall surface of the first seal element is positioned radially inwardly of the groove.

10. The implantable medical connector stack of claim 1, wherein the conductive ring contact element comprises an axially extending wall that projects over a shoulder of the first seal element and under a shoulder of the second seal element.

11. The implantable medical connector stack of claim 1, wherein a lead conductor is welded to the conductive ring contact element and is in electrical communication with a sealed housing of an implantable medical device.

12. An implantable medical connector stack having easy to install ring grooves for receiving contact springs comprising:
    a conductive ring contact element comprising a first axial side, a second axial side, and a bottom wall having a V-shape configuration;
    a first dielectric seal element in mechanical engagement with the first axial side of the conductive ring contact element;
    a second dielectric seal element in mechanical engagement with the second axial side of the conductive ring contact element; and
    wherein a ring groove for accommodating a canted coil spring is formed by the engagements between the conductive ring contact element and the first and second dielectric seal elements; and
    wherein at least part of the ring groove has a first side wall formed by at least one of the first dielectric seal element and the second dielectric seal element, and a portion of at least one of the dielectric seal elements projects into the conductive ring contact element.

13. The implantable medical connector stack of claim 12, wherein at least part of the ring groove has a second side wall formed by the other one of the first dielectric seal element and the second dielectric seal element.

14. The implantable medical connector stack of claim 12, further comprising a bore that is common to the conductive ring contact element and the first and second dielectric seal elements.

15. The implantable medical connector stack of claim 12, wherein the conductive ring contact element projects over a shoulder on each of the first and second dielectric seal elements.

16. The implantable medical connector stack of claim 12, wherein the conductive ring contact element projects under a shoulder on each of the first and second dielectric seal elements.

17. The implantable medical connector stack of claim 12, wherein the first dielectric seal element comprises an annulus comprising a projection.

18. The implantable medical connector stack of claim 12, wherein the stack is positioned inside an elastomeric or polymer header.

19. The implantable medical connector stack of claim 18, wherein the header is attached to a sealed housing of an implantable medical device.

20. The implantable medical connector stack of claim 12, wherein the conductive ring contact element comprises an axially extending wall that projects into a groove of the first dielectric seal element.

21. The implantable medical connector stack of claim 12, wherein the conductive ring contact element comprises an axially extending wall that projects over a shoulder of the first dielectric seal element and under a shoulder of the second dielectric seal element.

22. The implantable medical connector stack of claim 12, wherein a lead conductor is welded to the conductive ring contact element and is in electrical communication with a sealed housing of an implantable medical device.

23. The implantable medical connector stack of claim 12, further comprising two or more conductive ring contact elements.

24. A method for forming an implantable medical connector stack having easy to install ring grooves for receiving contact springs comprising:
   positioning a canted coil spring into a conductive ring contact element;
   positioning the conductive ring contact element into engagement with a first dielectric seal element;
   positioning the conductive ring contact element into engagement with a second dielectric seal element;
   wherein a groove comprising a bottom wall and two side walls is formed by the engagement between the conductive ring contact element and both the first and second dielectric seal elements; and
   wherein at least one of the two side walls is formed by part of the first dielectric seal element or the second dielectric seal element, and a portion of at least one of the dielectric seal elements projects into the conductive ring contact element.

25. The method for forming an implantable medical connector stack of claim 24, further comprising the step of placing a second conductive ring contact element into engagement with the second dielectric seal element.

26. The method for forming an implantable medical connector stack of claim 24, further comprising the step of placing the stack into a header made from a polymer or an elastomer material.

27. The method for forming an implantable medical connector stack of claim 24, further comprising the step of attaching the header to a sealed housing of an implantable medical device.

28. A method for forming a connector stack for an implantable medical device having reduced overall length comprising:
   inserting a tubular ring contact element into two adjacent seal ring elements to form a ring groove;
   placing a spring into said ring groove;
   wherein the seal ring elements form at least one side wall of two successive ring grooves, the seal ring elements each comprising an annular projection for forming a seal against a lead body; and
   wherein the tubular ring contact element is inserted into an interior shoulder of one of the two adjacent seal ring elements.

29. The method of claim 28, wherein the tubular ring contact element is inserted over an exterior shoulder of at least one of the two adjacent seal ring elements.

30. The method of claim 28, wherein the two adjacent seal ring elements each comprises an annulus and at least one projection defining an interior diameter.

* * * * *

UNITED STATES PATENT AND TRADEMARK OFFICE
CERTIFICATE OF CORRECTION

| | | |
|---|---|---|
| PATENT NO. | : 8,437,855 B2 | Page 1 of 1 |
| APPLICATION NO. | : 12/062895 | |
| DATED | : May 7, 2013 | |
| INVENTOR(S) | : Sjostedt et al. | |

It is certified that error appears in the above-identified patent and that said Letters Patent is hereby corrected as shown below:

On the Title Page, column 2, Item (57), abstract, delete "fore" and insert -- for --, therefor.

In the Specification

In column 6, line 22, delete "form" and insert -- from --, therefor.

In column 17, line 32, delete "Also." and insert -- Also, --, therefor.

Signed and Sealed this
Twenty-first Day of October, 2014

Michelle K. Lee
*Deputy Director of the United States Patent and Trademark Office*